(12) United States Patent
Efcavitch et al.

(10) Patent No.: US 10,041,110 B2
(45) Date of Patent: *Aug. 7, 2018

(54) METHODS AND APPARATUS FOR SYNTHESIZING NUCLEIC ACIDS

(71) Applicant: Molecular Assemblies, Inc., San Carlos, CA (US)

(72) Inventors: J. William Efcavitch, San Carlos, CA (US); Suhaib Siddiqi, Burlington, MA (US)

(73) Assignee: Molecular Assemblies, Inc., San Carlos, CA (US)

( * ) Notice: Subject to any disclaimer, the term of this patent is extended or adjusted under 35 U.S.C. 154(b) by 580 days.

This patent is subject to a terminal disclaimer.

(21) Appl. No.: 14/444,440

(22) Filed: Jul. 28, 2014

(65) Prior Publication Data

US 2014/0363851 A1 Dec. 11, 2014

Related U.S. Application Data

(63) Continuation of application No. 14/056,687, filed on Oct. 17, 2013, now Pat. No. 8,808,989.

(60) Provisional application No. 61/891,162, filed on Oct. 15, 2013, provisional application No. 61/807,327, filed on Apr. 2, 2013.

(51) Int. Cl.
| | |
|---|---|
| *C12Q 1/68* | (2018.01) |
| *C12Q 1/6844* | (2018.01) |
| *C12P 19/34* | (2006.01) |
| *C12N 9/12* | (2006.01) |
| *C12Q 1/6806* | (2018.01) |

(52) U.S. Cl.
CPC ......... *C12Q 1/6844* (2013.01); *C12N 9/1241* (2013.01); *C12N 9/1264* (2013.01); *C12P 19/34* (2013.01); *C12Q 1/6806* (2013.01); *C12Y 207/07019* (2013.01); *C12Y 207/07031* (2013.01); *Y02P 20/582* (2015.11)

(58) Field of Classification Search
CPC .................................................. C12Q 1/6844
USPC .................................................. 435/6.1, 91.1
See application file for complete search history.

(56) References Cited

U.S. PATENT DOCUMENTS

| | | | |
|---|---|---|---|
| 5,763,594 A | 6/1998 | Hiatt et al. | |
| 5,808,045 A | 9/1998 | Hiatt et al. | |
| 5,872,244 A | 2/1999 | Hiatt et al. | |
| 5,990,300 A | 11/1999 | Hiatt et al. | |
| 6,214,987 B1 | 4/2001 | Hiatt et al. | |
| 6,232,465 B1 | 5/2001 | Hiatt et al. | |
| 6,458,127 B1 | 10/2002 | Truckai et al. | |
| 6,664,079 B2 | 12/2003 | Ju et al. | |
| 7,208,172 B2 | 4/2007 | Birdsall et al. | |
| 7,279,563 B2 | 10/2007 | Kwiatkowski | |
| 7,414,116 B2 | 8/2008 | Milton et al. | |
| 7,494,797 B2 | 2/2009 | Mueller et al. | |
| 8,071,755 B2 | 12/2011 | Efcavitch et al. | |
| 8,133,669 B2 | 3/2012 | Lebedev et al. | |
| 8,152,839 B2 | 4/2012 | Buiser et al. | |
| 8,460,910 B2 | 6/2013 | Smith et al. | |
| 8,623,628 B2 | 1/2014 | Ost et al. | |
| 8,808,989 B1 * | 8/2014 | Efcavitch ................ | C12P 19/34 435/6.1 |
| 2004/0043396 A1 | 3/2004 | Mueller et al. | |
| 2005/0214759 A1 | 9/2005 | Wlassof et al. | |
| 2006/0127443 A1 | 6/2006 | Helmus | |
| 2007/0036905 A1 | 2/2007 | Kramer | |
| 2009/0186771 A1 | 7/2009 | Siddiqi et al. | |
| 2010/0304368 A1 * | 12/2010 | Cherkasov ............. | C07H 19/10 435/6.1 |
| 2011/0081647 A1 | 4/2011 | Siddiqi et al. | |
| 2011/0124529 A1 | 5/2011 | Brennan | |
| 2011/0201002 A1 | 8/2011 | Gelfand et al. | |
| 2012/0040340 A1 | 2/2012 | Efcavitch et al. | |
| 2013/0189743 A1 | 7/2013 | Balasubramanian et al. | |

FOREIGN PATENT DOCUMENTS

| | | | | |
|---|---|---|---|---|
| EP | 1 350 842 | A2 | 10/2003 | |
| WO | 92/10587 | A1 | 6/1992 | |
| WO | 1994/14972 | A1 | 7/1994 | |
| WO | 2005/005667 | A2 | 1/2005 | |
| WO | 2005/024010 | A1 | 3/2005 | |
| WO | 2005/026184 | A2 | 3/2005 | |
| WO | 2005/080605 | A2 | 9/2005 | |
| WO | 2006/007207 | A2 | 1/2006 | |
| WO | 20071022493 | A2 | 2/2007 | |
| WO | 2007/062160 | A2 | 5/2007 | |
| WO | WO-2007062160 | A2 * | 5/2007 | ............. C07H 21/00 |
| WO | 2007/147110 | A2 | 12/2007 | |
| WO | 2008/046602 | A2 | 4/2008 | |
| WO | 2008/046609 | A2 | 4/2008 | |
| WO | 2008/144315 | A1 | 11/2008 | |
| WO | 20081144544 | A1 | 11/2008 | |
| WO | 2009/124254 | A1 | 10/2009 | |
| WO | 2013013820 | A1 | 1/2013 | |

OTHER PUBLICATIONS

International Search Report and the Written Opinion of the International Searching Authority for International Application No. PCT/US2015/045729 dated Dec. 14, 2015 (16 Pages).

(Continued)

*Primary Examiner* — Jezia Riley
(74) *Attorney, Agent, or Firm* — Brown Rudnick LLP; Thomas C. Meyers

(57) ABSTRACT

The invention provides improved methods for synthesizing polynucleotides, such as DNA and RNA, using enzymes and specially designed nucleotide analogs. Using the methods of the invention, specific sequences of polynucleotides can be synthesized de novo, base by base, in an aqueous environment, without the use of a nucleic acid template. Because the nucleotide analogs have an unmodified 3' OH, i.e., as found in "natural" deoxyribose and ribose molecules, the analogs result in natural polynucleotides suitable for incorporation into biological systems.

23 Claims, 13 Drawing Sheets

(56) References Cited

OTHER PUBLICATIONS

Extended European Search Report dated Oct. 18, 2016 for European Application No. 16179096.9 (16 Pages).

Haynes, RD et al. A Chemically Synthesized Peptoid-Based Drag-Tag Enhances Free-Solution DNA Sequencing by Capillary Electrophoresis. Biopolymers. 2011, vol. 96, No. 5, pp. 702-707 (10 Pages).

International Search Report and Written Opinion of the International Search Authority dated Feb. 8, 2016 for International Application No. PCT/US2015/045730 (17 Pages).

Alexandrova LA, Jasko MV, Belobritskaya EE, Chudinov AV, Mityaeva ON, Nasedkina TV, Zasedatelev AS, Kukhanova MK. New triphosphate conjugates bearing reporter groups: labeling of DNA fragments for microarray analysis. Bioconjug Chem. May-Jun. 2007;18(3):886-93.

Auriol J, Chevrier D, Guesdon JL. Acetoxy-acetylaminofluorene-modified dGTP can be used to label oligonucleotides or DNA enzymatically. Mol Cell Probes Apr. 1997;11(2):113-21.

Beaucage SL, Caruthers, MH. Studies on Nucleotide Chemistry V. Deoxynucleoside Phosphoramidites—A New Class of Key Intermediates for Deoxypolynucleotide Synthesis. Tetrahedron Lett. 1981;22:1859-62.

Bi L, Kim DH, Ju J. Design and synthesis of a chemically cleavable fluorescent nucleotide, 3'-O-allyl-dGTP-allyl-bodipy-FL-510, as a reversible terminator for DNA sequencing by synthesis. J Am Chem Soc. Mar. 1, 2006;128(8):2542-3.

Bollum FJ. Terminal Deoxynucleotidyl Transferase. In: Boyer PD, editor. The Enzymes. vol. 10. New York: Academic Press; 1974. p. 148.

Boule J-B, Johnson E, Rougeo F, Papinicolaou. High-Level Expression of Murine Terminal Deoxynucleotidyl Transferase in *Escherichia coli* at Low Temparature and Overexpressing argU tRNA. Mol Biotechnology 1998;10:199-208.

Bowers et al., 2009, Virtual Terminator nucleotides for next generation DNA sequencing, Nat Methods 6:593-595 (and whole document).

Büssow K, Nordhoff E, Lübbert C, Lehrach H, Walter G. A human cDNA library for high-throughput protein expression screening. Genomics. Apr. 1, 2000;65(1):1-8.

Chang LMS, Bollum FJ. Molecular Biology of terminal Transferase. CRC Crit Rev Biochem. 1986;21(1):27-52.

Chow DC, Chilikoti A. Surface-initiated enzymatic polymerization of DNA. Langmuir 2007; 23:11712-7.

Chow DC, Lee W-K, Zauscher S, Chilikoti A. Enzymatic fabrication of DNA nanostructures: Extension of a self-assembled oligonucleotide monolayer on gold arrays. J Am Chem Soc 2005;127:14122-3.

Deibel MR, Liu CG, Barkley MD. Fluorimetric assay for terminal deoxynucleotidyl transferase activity. Anal Biochem 1985;144(2):336-46.

Delarue M, Boulé JB, Lescar J, Expert-Bezançon N, Jourdan N, Sukumar N, Rougeon F, Papanicolaou C. Crystal structures of a template-independent DNA polymerase: murine terminal deoxynucleotidyltransferase. EMBO J. 2002;21(3):427-39.

Figeys D, Renborg A, Dovichi NJ. Labeling of double-stranded DNA by ROX-dideoxycytosine triphosphate using terminal deoxynucleotidyl transferase and separation by capillary electrophoresis. Anal Chem 1994;66(23):4382-3.

Gouge J, Rosario S, Romain F, Beguin P, Delarue M. Structures of Intermediates along the Catalytic Cycle of Terminal Deoxynucleotidyltransferase: Dynamical Aspects of the Two-Metal Ion Mechanism. J Mol Biol. Nov. 15, 2013;425(22):4334-52.

Ikeda Y, Kawahara S-I, Yoshinari K, Fujita S, Taira K. Specifc 3'-terminal modification of DNA with a novel nucleoside analogue that allows a covalent linkage of a nuclear localization signal and enhancement of DNA stability. ChemBioChem 2005;6:297-303.

International Search Report and Written Opinion dated Aug. 27, 2014, for International Patent Application No. PCT/US2014/033881, filed Apr. 11, 2014 (13 pages).

International Search Report and Written Opinion dated Jan. 21, 2015, for International Patent Application No. PCT/IB2014/061673, filed May 23, 2014 (16 pages).

Kasahara Y, Kitadume S, Morihiro K, Kuwahara M, Ozaki H, Sawai H, Imanishi T, Obika S. Effect of 3'-end capping of aptamer with various 2',4'-bridged nucleotides: Enzymatic post-modification toward a practical use of polyclonal aptamers. Bioorg Med Chem Lett. Mar. 1, 2010;20(5):1626-9.

Kosuri S, Church GM. Large-scale de novo DNA synthesis: technologies and applications. Nat Methods. May 2014;11(5):499-507.

Kosuri S, Eroshenko N, Leproust EM, Super M, Way J, Li JB, Church GM. Scalable gene synthesis by selective amplification of DNA pools from high-fidelity microchips. Nat Biotechnol. Dec. 2010;28(12):1295-9.

Matteucci MD, Caruthers MH. Studies on Nucleotide Chemistry IV. Synthesis of Deoxyoligonucleotides on a Polymer Support. J. Amer. Chem. Soc. 1981;103:3185-91.

Meng Q, Kim DH, Bai X, Bi L, Turro NJ, Ju J. Design and synthesis of a photocleavable fluorescent nucleotide 3'-O-allyl-dGTP-PC-Bodipy-FL-510 as a reversible terminator for DNA sequencing by synthesis. J Org Chem. Apr. 14, 2006;71(8):3248-52.

Muller R, Drosdziok W, Rajewsky MF. Enzymatic synthesis of double-stranded DNA containing radioactively labeled O6-ethylguanine as the only modified base. Carcinogenesis 1981;2(4):321-7.

Sugiyama T, Ishii S, Saito K, Yamamoto J, Isogai T, Ota T. Preparation of sensitive and specific oligonucleotide probes tailed using terminal transferase and dITP. Biotechniques. Mar. 2000;28(3):486-90.

Sørensen RS, Okholm AH, Schaffert D, Bank Kodal AL, Gothelf KV, Kjems J. Enzymatic Ligation of Large Biomolecules to DNA. ACS Nano 2013;7(9):8098-104.

Tjong V, Yu H, Hucknall A, Rangarajan S, Chilkoti A. Amplified on-chip fluorescence detection of DNA hybridization by surface-initiated enzymatic polymerization. Anal Chem 2011;83:5153-59.

Zhou G, Sylvester JE, Wu D, Veach DR, Kron SJ. A magnetic bead-based protein kinase assay with dual detection techniques. Anal. Biochem. 2011;408:5-11.

European Search Report for Application No. EP 14 16 9758, with the Date of completion of the search of Jan. 12, 2015 (17 pages).

International Search Report and Written Opinion dated Sep. 30, 2014, for International Patent Application No. PCT/US2014/033811, filed Apr. 11, 2014 (12 pages).

Carr PA, Park JS, Lee Y-J, Yu T, Zhang S, Jacobson JM. Protein-mediated error correction for de novo DNA Synthesis. Nucleic Acids Research 2004;vol. 32(20):e162.

Chen F, Gaucher EA, Leal NA, Hutter D, Havemann SA, Govindarajan S, Ortlund EA, Benner SA. Reconstructed evolutionary adaptive paths give polymerases accepting reversible terminators for sequencing and SNP detection. Proc Natl Acad Sci U S A. Feb. 2, 2010;107(5):1948-53.

Damiani G, Scovassi I, Romagnoli S, Palla+ E, Bertazzoni U, Sgaramella V. Sequence analysis of heteropolymeric DNA synthesized in vitro by the enzyme terminal deoxynucleotidyl transferase and cloned in *Escherichia coli*. Nucleic Acids Res 1982;10(20):6401-10.

Gordon SR, Stanley EJ, Wolf S, Toland A, Wu SJ, Hadidi D, Mills JH, Baker D, Pultz IS, Siegel JB. Computational design of an ?-gliadin peptidase. J Am Chem Soc. Dec. 19, 2012;134(50):20513-20.

Hoard DE, Robert L, Ratliff D, Lloyd W, Newton Hayes F. Heteropolydeoxynucleotides synthesized with terminal deoxyribonucleotidyl transferase. J of Biol Chem 1969;244(19):5363-73.

Hutter D, Kim MJ, Karalkar N, Leal NA, Chen F, Guggenheim E, Visalakshi V, Olejnik J, Gordon S, Benner SA. Labeled nucleoside triphosphates with reversibly terminating aminoalkoxyl groups. Nucleosides Nucleotides Nucleic Acids. Nov. 2010;29(11):879-95.

Ju J, Kim DH, Bi L, Meng Q, Bai X, Li Z, Li X, Marma MS, Shi S, Wu J, Edwards JR, Romu A, Turro NJ. Four-color DNA sequencing by synthesis using cleavable fluorescent nucleotide reversible terminators. Proc Natl Acad Sci U S A. Dec. 26, 2006;103(52):19635-40.

(56) References Cited

OTHER PUBLICATIONS

Kuan WL, Joy J, Mee NF, Perlyn KZ, Wen TS, Nguen T, James J, Chai E, Flowtow H, Crasta S, Chua K, Peng NS, Hill J. Generation of active bovine Terminal Deoxynucleotidyl Transferase (TdT) in E. coli. Biochem. Insights. 2010;3:41-6.

Li X, Traganos F, Melamed MR, Darzynkiewicz Z. Single-step procedure for labeling DNA strand breaks with fluorescein- or BODIPY-conjugated deoxynucleotides: detection of apoptosis and bromodeoxyuridine incorporation. Cytometry 1995;20(2):172-80.

Life Technologies [Internet]. Carlsbad: Life Technologies Inc.; c 2013. Oligo Minimum Yield Guarantee; [cited Dec. 1, 2013]. Available from: http://www.lifetechnologies.com/us/en/home/products-and-services/product-types/primers-oligos-nucleotides/invitrogen-custom-dna-oligos/oligo-ordering-details/oligo-minimum-yield-guarantee.html.

Minhaz Ud-Dean SM. A theoretical model for template-free synthesis of long DNA sequence. Syst Synth Biol. 2009;2:67-73.

Nitta Y, Ogino M, Yoshimura Y, Fujimoto K. Synthesis of a photoresponsive alpha-dideoxyuridine triphosphate derivative. Nucleic Acids Symp Ser (Oxf). 2008;(52):293-4.

Romain F, Barbosa I, Gouge J, Rougeon F, Delarue M. Conferring a template-dependent polymerase activity to terminal deoxynucleotidyltransferase by mutations in the Loop1 region. Nucleic Acids Res. 2009;37(14):4642-56.

Schott H, Schrade H. Single-step elongation of oligodeoxynucleotides using terminal deoxynucleotidyl transferase. Eur J Biochem 1984;143:613-20.

Siegel JB, Zanghellini A, Lovick HM, Kiss G, Lambert AR, St Clair JL, Gallaher JL, Hilvert D, Gelb MH, Stoddard BL, Houk KN, Michael FE, Baker D. Computational design of an enzyme catalyst for a stereoselective bimolecular Diels-Alder reaction. Science. Jul. 16, 2010;329(5989):309-13.

Sleight SC, Bartley BA, Lieviant JA, Sauro HM. In-Fusion BioBrick assembly and re-engineering. Nucleic Acids Res. May 2010;38(8):2624-36.

Wu SJ, Eiben CB, Carra JH, Huang I, Zong D, Liu P, Wu CT, Nivala J, Dunbar J, Huber T, Senft J, Schokman R, Smith MD, Mills JH, Friedlander AM, Baker D, Siegel JB. Improvement of a potential anthrax therapeutic by computational protein design. J Biol Chem. Sep. 16, 2011;286(37):32586-92.

Yang B, Gathy KN, Coleman MS. Mutational Analysis of Residues in the Nucleotide Binding Domain of Human Terminal Deoxynucleotidyl Transferase. J. Mol. Biol. Apr. 22, 1994; 269(16):11859-68.

International Search Report and Written Opinion for PCT/US2014/033811, dated Sep. 30, 2014.

Barone AD, Chen C, McGall GH, Rafii K, Buzby PR, Dimeo JJ. Novel nucleoside triphosphate analogs for the enzymatic labeling of nucleic acids. Nucleoside, Nucleotides and Nucleic Acids 2001;20(4-7):1141-5.

Bentley DR, Balasubramanian S, Swerdlow HP, Smith GP, Milton J, Brown CG, et al. Accurate whole human genome sequencing using reversible terminator chemistry.Nature 2008;456:53-9.

Bowers et al., Molecular Biology of Terminal Transferase, Nature Methods, vol. 6, (2009) p. 593-95.

Bowers J, Mitchell J, Beer E, Buzby PR, Causey M, Efcavitch JW, Jarosz M, Krzymanska-Olejnik E, Kung L, Lipson D, Lowman GM, Marappan S, McInerney P, Plat A, Roy A, Siddiqi SM, Steinmann K, Thompson JF. Virtual terminator nucleotides for next-generation DNA sequencing. Nature Methods 2009;6(8):593-95.

Carlson R, The changing economics of DNA synthesis. Nature Biotechnol. 2009;27:1091-4.

Caruthers MH. Gene Synthesis Machines: DNA chemistry and its Uses. Science 1985;230(4723):281-5.

Efcavitch JW. Automated System for the Optimized Chemical Synthesis of Oligodeoxyribonucleotides. In: Schlesinger DH, editor. Macromolecular Sequencing and Synthesis. New York: Alan R Liss, Inc.; 1988. p. 221-34.

Flickinger JL, Gebeyehu G, Haces A, Rashtchian A. Differential incorporation of biotinylated nucleotides by terminal deoxynucleotidyl transferase. Nucleic Acids Res 1992;20(9):2382.

Guo J, Xu N, Li Z, Zhang S, Wu J, Hyun Kim D, Marma MS, Meng Q, Cao H, Li X, Shi S, Yu L, Kalachikov S, Russo JJ, Turro NJ, Ju J. Four-color DNA sequencing with 3'-Omodifiednucleotide reversible terminators and chemically cleavable fluorescent dideoxynucleotides. Proc. Natl. Acad. Sci. USA 2008;105:9145-50.

Horakova P, Macickova-Cahova H, Pivonkova H, Spacek J, Havran L, Hocek M, Fojta M. Tail-labelling of DNA probes using modified deoxynucleotide triphosphates and terminal deoxynucleotidyl transferase. Application in electrochemical DNA hybridization and protein-DNA binding assays. Org Biomol Chem 2011;9(5):1366-71.

Lashkari DA, Hunicke-Smith SP, Norgren RM, Davis RW, Brennan T. An automated multiplex oligonucleotide synthesizer: development of high-throughput, low-cost DNA synthesis. Proc Natl Acad Sci USA. 1995;92(17):7912-15.

Leconte AM, Patel MP, Sass LE, McInerney P, Jarosz M, Kung L, Bowers JL, Buzby PR, Efcavitch JW, Romesberg FE. Directed evolution of DNA polymerases for next generation sequencing. Angew Chem Int Ed Engl. 2010;49(34):5921-24.

Lee CC, Snyder TM, Quake SR. A Microfluidic Oligonucleotide Synthesizer. Nucleic Acids Res 2010;38:2514-21.

LeProust EM, Peck BJ, Spirin K, MCuen HB, Moore B, Namsaraev E, Caruthers MH. Synthesis of high-quality libraries of long (150mer) oligonucleotides by a novel depurination controlled process. Nucleic Acids Res 2010;38(8):2522-40.

LeProust et al., Synthesis of high-quality libraries of long (150mer) oligonucleotides by a novel depurination controlled process. Nucleic Acids Res., vol. 38(8), p. 2522-2540, (2010).

Litosh VA, Wu W, Stupi BP, Wang J, Morris SE, Hersh N, Metzker ML. Improved nucleotide selectivity and termination of 3?-OH unblocked reversible terminators by molecular tuning of 2-nitrobenzyl alkylated HOMedU triphosphates. Nucleic Acid Res 2011;39:e39.

Matzas M, Stahler PF, Kefer N, Siebelt N, Boisguerin V, Leonard JT, et al. Next Generation Gene Synthesis by targeted retrieval of bead-immobilized, sequence verified DNA clones from a high throughput pyrosequencing device. Nat Biotechnol. 2010;28(12)1291-1294.

Metzker ML, Raghavachari R, Richards S, Jacutin SE, Civitello A, Burgess K, Gibbs RA. Termination of DNA synthesis by novel 3'-modifieddeoxyribonucleoside 5'-triphosphates. Nucleic Acids Res 1994;22:4259-67.

Motea EA, Berdis AJ. Terminal deoxynucleotidyl transferase: The story of a misguided DNA polymerase. Biochimica et Biophysica Acta 2010;1804:1151-6.

Zahid M, Kim B, Hussain R, Amin R, Park SH. DNA nanotechnology: a future perspective. Nanoscales Res Lett. 2013;8:119-32.

* cited by examiner n = 2 or 3
X = O, NH, CH$_2$, S

TCEP or DTT n = 2 or 3
X = O, NH, CH$_2$, S

TCEP or DTT n = 2 or 3
X = O, NH, CH₂, S n = 2 or 3
X = O, NH, CH$_2$, S n = 2 or 3
X = O, NH, CH$_2$, S

SEQUENCE LISTING

```
<160> NUMBER OF SEQ ID NOS: 6

<210> SEQ ID NO 1
<211> LENGTH: 520
<212> TYPE: PRT
<213> ORGANISM: Bos taurus

<400> SEQUENCE: 1

Met Ala Gln Gln Arg Gln His Gln Arg Leu Pro Met Asp Pro Leu Cys
1               5                   10                  15

Thr Ala Ser Ser Gly Pro Arg Lys Lys Arg Pro Arg Gln Val Gly Ala
                20                  25                  30

Ser Met Ala Ser Pro Pro His Asp Ile Lys Phe Gln Asn Leu Val Leu
            35                  40                  45

Phe Ile Leu Glu Lys Lys Met Gly Thr Thr Arg Arg Asn Phe Leu Met
    50                  55                  60

Glu Leu Ala Arg Arg Lys Gly Phe Arg Val Glu Asn Glu Leu Ser Asp
65                  70                  75                  80

Ser Val Thr His Ile Val Ala Glu Asn Asn Ser Gly Ser Glu Val Leu
                85                  90                  95

Glu Trp Leu Gln Val Gln Asn Ile Arg Ala Ser Ser Gln Leu Glu Leu
                100                 105                 110

Leu Asp Val Ser Trp Leu Ile Glu Ser Met Gly Ala Gly Lys Pro Val
            115                 120                 125

Glu Ile Thr Gly Lys His Gln Leu Val Val Arg Thr Asp Tyr Ser Ala
    130                 135                 140

Thr Pro Asn Pro Gly Phe Gln Lys Thr Pro Pro Leu Ala Val Lys Lys
145                 150                 155                 160

Ile Ser Gln Tyr Ala Cys Gln Arg Lys Thr Thr Leu Asn Asn Tyr Asn
                165                 170                 175
```

```
His Ile Phe Thr Asp Ala Phe Glu Ile Leu Ala Glu Asn Ser Glu Phe
            180                 185                 190

Lys Glu Asn Glu Val Ser Tyr Val Thr Phe Met Arg Ala Ala Ser Val
        195                 200                 205

Leu Lys Ser Leu Pro Phe Thr Ile Ile Ser Met Lys Asp Thr Glu Gly
    210                 215                 220

Ile Pro Cys Leu Gly Asp Lys Val Lys Cys Ile Ile Glu Glu Ile Ile
225                 230                 235                 240

Glu Asp Gly Glu Ser Ser Glu Val Lys Ala Val Leu Asn Asp Glu Arg
                245                 250                 255

Tyr Gln Ser Phe Lys Leu Phe Thr Ser Val Phe Gly Val Gly Leu Lys
            260                 265                 270

Thr Ser Glu Lys Trp Phe Arg Met Gly Phe Arg Ser Leu Ser Lys Ile
        275                 280                 285

Met Ser Asp Lys Thr Leu Lys Phe Thr Lys Met Gln Lys Ala Gly Phe
    290                 295                 300

Leu Tyr Tyr Glu Asp Leu Val Ser Cys Val Thr Arg Ala Glu Ala Glu
305                 310                 315                 320

Ala Val Gly Val Leu Val Lys Glu Ala Val Trp Ala Phe Leu Pro Asp
                325                 330                 335

Ala Phe Val Thr Met Thr Gly Gly Phe Arg Arg Gly Lys Lys Ile Gly
            340                 345                 350

His Asp Val Asp Phe Leu Ile Thr Ser Pro Gly Ser Ala Glu Asp Glu
        355                 360                 365

Glu Gln Leu Leu Pro Lys Val Ile Asn Leu Trp Glu Lys Lys Gly Leu
    370                 375                 380

Leu Leu Tyr Tyr Asp Leu Val Glu Ser Thr Phe Glu Lys Phe Lys Leu
385                 390                 395                 400

Pro Ser Arg Gln Val Asp Thr Leu Asp His Phe Gln Lys Cys Phe Leu
                405                 410                 415

Ile Leu Lys Leu His His Gln Arg Val Asp Ser Ser Lys Ser Asn Gln
            420                 425                 430

Gln Glu Gly Lys Thr Trp Lys Ala Ile Arg Val Asp Leu Val Met Cys
        435                 440                 445

Pro Tyr Glu Asn Arg Ala Phe Ala Leu Leu Gly Trp Thr Gly Ser Arg
    450                 455                 460

Gln Phe Glu Arg Asp Ile Arg Arg Tyr Ala Thr His Glu Arg Lys Met
465                 470                 475                 480

Met Leu Asp Asn His Ala Leu Tyr Asp Lys Thr Lys Arg Val Phe Leu
                485                 490                 495

Lys Ala Glu Ser Glu Glu Glu Ile Phe Ala His Leu Gly Leu Asp Tyr
            500                 505                 510

Ile Glu Pro Trp Glu Arg Asn Ala
        515                 520

<210> SEQ ID NO 2
<211> LENGTH: 1923
<212> TYPE: DNA
<213> ORGANISM: Bos taurus

<400> SEQUENCE: 2
ctcttctgga gataccactt gatggcacag cagaggcagc atcagcgtct tcccatggat      60
ccgctgtgca cagcctcctc aggccctcgg aagaagagac ccaggcaggt gggtgcctca     120
atggcctccc ctcctcatga catcaagttt caaaatttgg tcctcttcat tttggagaag     180
```

| | |
|---|---|
| aaaatgggaa ccacccgcag aaacttcctc atggagctgg ctcgaaggaa aggtttcagg | 240 |
| gttgaaaatg agctcagtga ttctgtcacc cacattgtag cagaaaacaa ctctggttca | 300 |
| gaggttctcg agtggcttca ggtacagaac ataagagcca gctcgcagct agaactcctt | 360 |
| gatgtctcct ggctgatcga agtatggga gcaggaaaac cagtggagat acaggaaaa | 420 |
| caccagcttg ttgtgagaac agactattca gctaccccaa acccaggctt ccagaagact | 480 |
| ccaccacttg ctgtaaaaaa gatctcccag tacgcgtgtc aaagaaaaac cactttgaac | 540 |
| aactataacc acatattcac ggatgccttt gagatactgg ctgaaaattc tgagtttaaa | 600 |
| gaaaatgaag tctcttatgt gacatttatg agagcagctt ctgtacttaa atctctgcca | 660 |
| ttcacaatca tcagtatgaa ggatacagaa ggaattccct gcctggggga caaggtgaag | 720 |
| tgtatcatag aggaaattat tgaagatgga gaaagttctg aagttaaagc tgtgttaaat | 780 |
| gatgaacgat atcagtcctt caaactcttt acttctgttt ttggagtggg actgaagaca | 840 |
| tctgagaaat ggttcaggat ggggttcaga tctctgagta aataatgtc agacaaaacc | 900 |
| ctgaaattca caaaaatgca gaaagcagga tttctctatt atgaagacct tgtcagctgc | 960 |
| gtgaccaggg ccgaagcaga ggcggttggc gtgctggtta agaggctgt gtgggcattt | 1020 |
| ctgccggatg cctttgtcac catgacagga ggattccgca ggggtaagaa gattgggcat | 1080 |
| gatgtagatt ttttaattac cagcccagga tcagcagagg atgaagagca acttttgcct | 1140 |
| aaagtgataa acttatggga aaaaaggga ttacttttat attatgacct tgtggagtca | 1200 |
| acatttgaaa agttcaagtt gccaagcagg caggtggata ctttagatca ttttcaaaaa | 1260 |
| tgctttctga ttttaaaatt gcaccatcag agagtagaca gtagcaagtc caaccagcag | 1320 |
| gaaggaaaga cctggaaggc catccgtgtg gacctggtta tgtgccccta cgagaaccgt | 1380 |
| gcctttgccc tgctaggctg gactggctcc cggcagtttg agagagacat ccggcgctat | 1440 |
| gccacacacg agcggaagat gatgctggat aaccacgctt tatatgacaa gaccaagagg | 1500 |
| gtatttctca aagcggaaag tgaagaagaa atctttgcac atctgggatt ggactacatt | 1560 |
| gaaccatggg aaagaaatgc ttaggagaaa gctgtcaact tttttctttt ctgttctttt | 1620 |
| tttcaggtta gacaaattat gcttcatatt ataatgaaag atgccttagt caagtttggg | 1680 |
| attctttaca ttttaccaag atgtagattg cttctagaaa taagtagttt tggaaacgtg | 1740 |
| atcaggcacc ccctgggtta tgctctggca agccatttgc aggactgatg tgtagaactc | 1800 |
| gcaatgcatt ttccatagaa acagtgttgg aattggtggc tcatttccag ggaagttcat | 1860 |
| caaagcccac tttgcccaca gtgtagctga aatactgtat acttgccaat aaaaatagga | 1920 |
| aac | 1923 |

<210> SEQ ID NO 3
<211> LENGTH: 465
<212> TYPE: PRT
<213> ORGANISM: Escherichia coli

<400> SEQUENCE: 3

Met Phe Thr Arg Val Ala Asn Phe Cys Arg Lys Val Leu Ser Arg Glu
1               5                   10                  15

Glu Ser Glu Ala Glu Gln Ala Val Ala Arg Pro Gln Val Thr Val Ile
            20                  25                  30

Pro Arg Glu Gln His Ala Ile Ser Arg Lys Asp Ile Ser Glu Asn Ala
        35                  40                  45

Leu Lys Val Met Tyr Arg Leu Asn Lys Ala Gly Tyr Glu Ala Trp Leu
    50                  55                  60

-continued

Val Gly Gly Gly Val Arg Asp Leu Leu Leu Gly Lys Lys Pro Lys Asp
65                  70                  75                  80

Phe Asp Val Thr Thr Asn Ala Thr Pro Glu Gln Val Arg Lys Leu Phe
            85                  90                  95

Arg Asn Cys Arg Leu Val Gly Arg Phe Arg Leu Ala His Val Met
            100                 105                 110

Phe Gly Pro Glu Ile Ile Glu Val Ala Thr Phe Arg Gly His His Glu
            115                 120                 125

Gly Asn Val Ser Asp Arg Thr Thr Ser Gln Arg Gly Gln Asn Gly Met
    130                 135                 140

Leu Leu Arg Asp Asn Ile Phe Gly Ser Ile Glu Glu Asp Ala Gln Arg
145                 150                 155                 160

Arg Asp Phe Thr Ile Asn Ser Leu Tyr Tyr Ser Val Ala Asp Phe Thr
                165                 170                 175

Val Arg Asp Tyr Val Gly Gly Met Lys Asp Leu Lys Asp Gly Val Ile
                180                 185                 190

Arg Leu Ile Gly Asn Pro Glu Thr Arg Tyr Arg Glu Asp Pro Val Arg
        195                 200                 205

Met Leu Arg Ala Val Arg Phe Ala Ala Lys Leu Gly Met Arg Ile Ser
    210                 215                 220

Pro Glu Thr Ala Glu Pro Ile Pro Arg Leu Ala Thr Leu Leu Asn Asp
225                 230                 235                 240

Ile Pro Pro Ala Arg Leu Phe Glu Glu Ser Leu Lys Leu Leu Gln Ala
                245                 250                 255

Gly Tyr Gly Tyr Glu Thr Tyr Lys Leu Leu Cys Glu Tyr His Leu Phe
                260                 265                 270

Gln Pro Leu Phe Pro Thr Ile Thr Arg Tyr Phe Thr Glu Asn Gly Asp
        275                 280                 285

Ser Pro Met Glu Arg Ile Ile Glu Gln Val Leu Lys Asn Thr Asp Thr
    290                 295                 300

Arg Ile His Asn Asp Met Arg Val Asn Pro Ala Phe Leu Phe Ala Ala
305                 310                 315                 320

Met Phe Trp Tyr Pro Leu Leu Glu Thr Ala Gln Lys Ile Ala Gln Glu
                325                 330                 335

Ser Gly Leu Thr Tyr His Asp Ala Phe Ala Leu Ala Met Asn Asp Val
                340                 345                 350

Leu Asp Glu Ala Cys Arg Ser Leu Ala Ile Pro Lys Arg Leu Thr Thr
            355                 360                 365

Leu Thr Arg Asp Ile Trp Gln Leu Gln Leu Arg Met Ser Arg Arg Gln
370                 375                 380

Gly Lys Arg Ala Trp Lys Leu Leu Glu His Pro Lys Phe Arg Ala Ala
385                 390                 395                 400

Tyr Asp Leu Leu Ala Leu Arg Ala Glu Val Glu Arg Asn Ala Glu Leu
                405                 410                 415

Gln Arg Leu Val Lys Trp Trp Gly Glu Phe Gln Val Ser Ala Pro Pro
            420                 425                 430

Asp Gln Lys Gly Met Leu Asn Glu Leu Asp Glu Pro Ser Pro Arg
            435                 440                 445

Arg Arg Thr Arg Arg Pro Arg Lys Arg Ala Pro Arg Arg Glu Gly Thr
    450                 455                 460

Ala
465

<210> SEQ ID NO 4
<211> LENGTH: 1398
<212> TYPE: DNA
<213> ORGANISM: Escherichia coli

<400> SEQUENCE: 4

```
atttttaccc gagtcgctaa tttttgccgc aaggtgctaa gccgcgagga aagcgaggct      60
gaacaggcag tcgcccgtcc acaggtgacg gtgatcccgc gtgagcagca tgctatttcc     120
cgcaaagata tcagtgaaaa tgccctgaag gtaatgtaca ggctcaataa agcgggatac     180
gaagcctggc tggttggcgg cggcgtgcgc gacctgttac ttggcaaaaa gccgaaagat     240
tttgacgtaa ccactaacgc cacgcctgag caggtgcgca aactgttccg taactgccgc     300
ctggtgggtc gccgtttccg tctggctcat gtaatgtttg gcccggagat tatcgaagtt     360
gcgaccttcc gtggacacca cgaaggtaac gtcagcgacc gcacgacctc caacgcggg     420 caaaacggca tgttgctgcg cgacaacatt ttcggctcca tcgaagaaga cgcccagcgc     480
cgcgatttca ctatcaacag cctgtattac agcgtagcgg attttaccgt ccgtgattac     540
gttggcggca tgaaggatct gaaggacggc gttatccgtc tgattggtaa cccggaaacg     600
cgctaccgtg aagatccggt acgtatgctg cgcgcggtac gttttgccgc caaattgggt     660
atgcgcatca gcccggaaac cgcagaaccg atccctcgcc tcgctaccct gctgaacgat     720
atcccaccgg cacgcctgtt tgaagaatcg cttaaactgc tacaagcggg ctacggttac     780
gaaacctata agctgttgtg tgaatatcat ctgttccagc cgctgttccc gaccattacc     840
cgctacttca cggaaaatgg cgacagcccg atggagcgga tcattgaaca ggtgctgaag     900 ataccgata cgcgtatcca taacgatatg cgcgtgaacc cggcgttcct gtttgccgcc     960
atgttctggt acccactgct ggagacggca cagaagatcg cccaggaaag cggcctgacc    1020
tatcacgacg ctttcgcgct ggcgatgaac gacgtgctgg acgaagcctg ccgttcactg    1080
gcaatcccga aacgtctgac gacattaacc cgcgatatct ggcagttgca gttgcgtatg    1140
tcccgtcgtc agggtaaacg cgcatggaaa ctgctggagc atcctaagtt ccgtgcggct    1200
tatgacctgt tggccttgcg agctgaagtt gagcgtaacg ctgaactgca gcgtctggtg    1260
aaatggtggg gtgagttcca ggtttccgcg ccaccagacc aaaaagggat gctcaacgag    1320
ctggatgaag aaccgtcacc gcgtcgtcgt actcgtcgtc cacgcaaacg cgcaccacgt    1380
cgtgagggta ccgcatga                                                  1398
```

<210> SEQ ID NO 5
<211> LENGTH: 349
<212> TYPE: PRT
<213> ORGANISM: Escherichia coli

<400> SEQUENCE: 5

Gly Ser His Met Ser Tyr Gln Lys Val Pro Asn Ser His Lys Glu Phe
1               5                   10                  15

Thr Lys Phe Cys Tyr Glu Val Tyr Asn Glu Ile Lys Ile Ser Asp Lys
            20                  25                  30

Glu Phe Lys Glu Lys Arg Ala Ala Leu Asp Thr Leu Arg Leu Cys Leu
        35                  40                  45

Lys Arg Ile Ser Pro Asp Ala Glu Leu Val Ala Phe Gly Ser Leu Glu
    50                  55                  60

Ser Gly Leu Ala Leu Lys Asn Ser Asp Met Asp Leu Cys Val Leu Met
65                  70                  75                  80

Asp Ser Arg Val Gln Ser Asp Thr Ile Ala Leu Gln Phe Tyr Glu Glu
             85                  90                  95

Leu Ile Ala Glu Gly Phe Glu Gly Lys Phe Leu Gln Arg Ala Arg Ile
        100                 105                 110

Pro Ile Ile Lys Leu Thr Ser Asp Thr Lys Asn Gly Phe Gly Ala Ser
        115                 120                 125

Phe Gln Cys Asp Ile Gly Phe Asn Asn Arg Leu Ala Ile His Asn Thr
        130                 135                 140

Leu Leu Leu Ser Ser Tyr Thr Lys Leu Asp Ala Arg Leu Lys Pro Met
145                 150                 155                 160

Val Leu Leu Val Lys His Trp Ala Lys Arg Lys Gln Ile Asn Ser Pro
                165                 170                 175

Tyr Phe Gly Thr Leu Ser Ser Tyr Gly Tyr Val Leu Met Val Leu Tyr
                180                 185                 190

Tyr Leu Ile His Val Ile Lys Pro Pro Val Phe Pro Asn Leu Leu Leu
                195                 200                 205

Ser Pro Leu Lys Gln Glu Lys Ile Val Asp Gly Phe Asp Val Gly Phe
210                 215                 220

Asp Asp Lys Leu Glu Asp Ile Pro Pro Ser Gln Asn Tyr Ser Ser Leu
225                 230                 235                 240

Gly Ser Leu Leu His Gly Phe Phe Arg Phe Tyr Ala Tyr Lys Phe Glu
                245                 250                 255

Pro Arg Glu Lys Val Val Thr Phe Arg Arg Pro Asp Gly Tyr Leu Thr
                260                 265                 270

Lys Gln Glu Lys Gly Trp Thr Ser Ala Thr Glu His Thr Gly Ser Ala
                275                 280                 285

Asp Gln Ile Ile Lys Asp Arg Tyr Ile Leu Ala Ile Glu Asp Pro Phe
        290                 295                 300

Glu Ile Ser His Asn Val Gly Arg Thr Val Ser Ser Ser Gly Leu Tyr
305                 310                 315                 320

Arg Ile Arg Gly Glu Phe Met Ala Ala Ser Arg Leu Leu Asn Ser Arg
                325                 330                 335

Ser Tyr Pro Ile Pro Tyr Asp Ser Leu Phe Glu Glu Ala
                340                 345

<210> SEQ ID NO 6
<211> LENGTH: 1047
<212> TYPE: DNA
<213> ORGANISM: Escherichia coli

<400> SEQUENCE: 6
ggcagccata tgagctatca gaaagtgccg aacagccata agaatttac caaattttgc      60 tatgaagtgt ataacgaaat taaaattagc gataaagaat ttaaagaaaa acgcgcggcg    120
ctggatcccc tgcgcctgtg cctgaaacgc attagcccgg atgcggaact ggtggcgttt    180
ggcagcctgg aaagcggcct ggcgctgaaa acagcgata tggatctgtg cgtgctgatg     240
gatagccgcg tgcagagcga taccattgcg ctgcagtttt atgaagaact gattgcggaa    300
ggctttgaag gcaaatttct gcagcgcgcg cgcattccga ttattaaact gaccagcgat    360
accaaaaacg gctttggcgc gagctttcag tgcgatattg gctttaacaa ccgcctggcg    420
attcataaca ccctgctgct gagcagctat accaaactgg atgcgcgcct gaaaccgatg    480
gtgctgctgg tgaaacattg ggcgaaacgc aaacagatta acagcccgta ttttggcacc    540
ctgagcagct atggctatgt gctgatggtg ctgtattatc tgattcatgt gattaaaccg    600

```
ccggtgtttc cgaacctgct gctgagcccg ctgaaacagg aaaaaattgt ggatggcttt      660
gatgtgggct ttgatgataa actggaagat attccgccga gccagaacta tagcagcctg      720
ggcagcctgc tgcatggctt ttttcgcttt tatgcgtata aatttgaacc gcgcgaaaaa      780
gtggtgacct ttcgccgccc ggatggctat ctgaccaaac aggaaaaagg ctggaccagc      840
gcgaccgaac ataccggcag cgcggatcag attattaaag atcgctatat tctggcgatt      900
gaagatccgt ttgaaattag ccataacgtg ggccgcaccg tgagcagcag cggcctgtat      960
cgcattcgcg gcgaatttat ggcggcgagc cgcctgctga acagccgcag ctatccgatt     1020
ccgtatgata gcctgtttga agaagcg                                         1047
```

METHODS AND APPARATUS FOR SYNTHESIZING NUCLEIC ACIDS

RELATED APPLICATIONS

This application is a continuation of U.S. patent application Ser. No. 14/056,687, filed Oct. 17, 2013, which claims priority to U.S. Provisional Application Nos. 61/807,327, filed Apr. 2, 2013, and 61/891,162, filed Oct. 15, 2013, all of which are incorporated by reference in their entireties.

FIELD OF THE INVENTION

The invention relates to methods and apparatus for synthesizing polynucleotides (de novo) with a desired sequence and without the need for a template. As such, the invention provides the capacity to make libraries of polynucleotides of varying sequence and varying length for research, genetic engineering, and gene therapy.

BACKGROUND

Genetic engineering requires tools for determining the content of genetic material as well as tools for constructing desired genetic materials. The tools for determining the content of genetic material have made it possible to sequence an entire human genome in about one day for under $1,000. (See Life Technologies, *Press Release: Benchtop Ion Proton™ Sequencer*, Jan. 10, 2012). In contrast, the tools for constructing desired genetic materials, e.g., de novo DNA synthesis, have not improved at the same pace. As a point of reference, over the past 25 years, the cost (per base) of de novo small nucleic acid synthesis has dropped 10-fold, while the cost (per base) of nucleic acid sequencing has dropped over 10,000,000-fold. The lack of progress in DNA synthesis now limits the pace of translational genomics, i.e., whereby the role of individual sequence variations are determined and used to develop therapeutic treatments.

Currently, most de novo nucleic acid sequences are synthesized using solid phase phosphoramidite-techniques developed more than 30 years ago. The technique involves the sequential de-protection and synthesis of sequences built from phosphoramidite reagents corresponding to natural (or non-natural) nucleic acid bases. Phosphoramidite nucleic acid synthesis is length-limited, however, in that nucleic acids greater than 200 base pairs (bp) in length experience high rates of breakage and side reactions. Additionally, phosphoramidite synthesis produces toxic by-products, and the disposal of this waste limits the availability of nucleic acid synthesizers, and increases the costs of contract oligo production. (It is estimated that the annual demand for oligonucleotide synthesis is responsible for greater than 300,000 gallons of hazardous chemical waste, including acetonitrile, trichloroacetic acid, toluene, tetrahydrofuran, and pyridine. See LeProust et al., *Nucleic Acids Res.*, vol. 38(8), p. 2522-2540, (2010), incorporated by reference herein in its entirety). Thus, there is a need for more efficient and cost-effective methods for oligonucleotide synthesis.

SUMMARY

The invention provides improved methods for nucleic acid synthesis. Methods of the invention provide faster and longer de novo synthesis of polynucleotides. As such, the invention dramatically reduces the overall cost of synthesizing custom nucleic acids. Methods of the invention are directed to template-independent synthesis of polynucleotides by using a nucleotidyl transferase enzyme to incorporate nucleotide analogs having an unmodified 3' hydroxyl and a cleavable terminating group. Because of the terminating group, synthesis pauses with the addition of each new base, whereupon the terminating group is cleaved, leaving a polynucleotide that is essentially identical to a naturally occurring nucleotide (i.e., is recognized by the enzyme as a substrate for further nucleotide incorporation).

The invention additionally includes an apparatus that utilizes methods of the invention for the production of custom polynucleotides. An apparatus of the invention includes one or more bioreactors providing aqueous conditions and a plurality of sources of nucleotide analogs. The bioreactor may be e.g., a reservoir, a flow cell, or a multi-well plate. Starting from a solid support, the polynucleotides are grown in the reactor by adding successive nucleotides via the natural activity of a nucleotidyl transferase, e.g., a terminal deoxynucleotidyl transferase (TdT) or any other enzyme which elongates DNA or RNA strands without template direction. Upon cleavage of the terminating group, a natural polynucleotide is exposed on the solid support. Once the sequence is complete, the support is cleaved away, leaving a polynucleotide essentially equivalent to that found in nature. In some embodiments, the apparatus is designed to recycle nucleotide analog solutions by recovering the solutions after nucleotide addition and reusing solutions for subsequence nucleotide addition. Thus, less waste is produced, and the overall cost per base is reduced as compared to state-of-the-art methods.

Other aspects of the invention are apparent to the skilled artisan upon consideration of the following figures and detailed description.

DETAILED DESCRIPTION

Figure 1A:
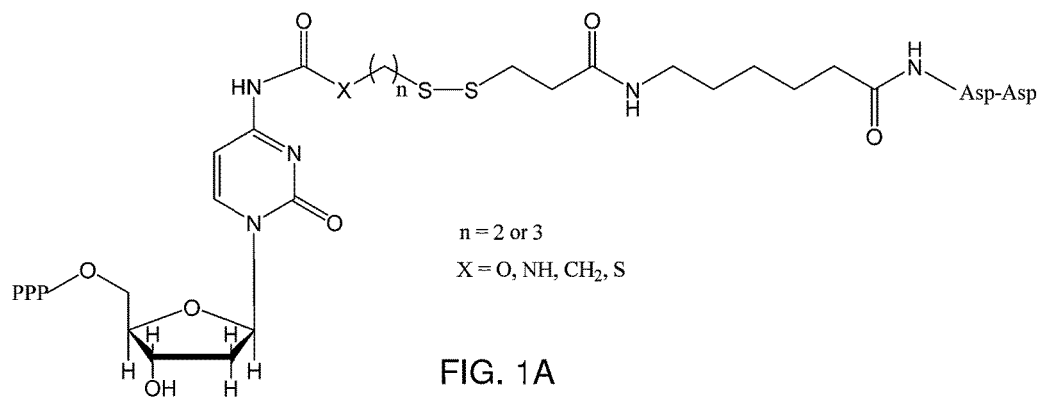
FIG. 1A shows a genus of deoxycytidine triphosphate (dCTP) analogs having a cleavable terminator linked at the N-4 position.

The invention provides improved methods for synthesizing polynucleotides, such as DNA and RNA, using enzymes and nucleic acid analogs. Using the disclosed methods, specific sequences of polynucleotides can be synthesized de novo, base by base, in an aqueous environment, without the use of a nucleic acid template. Additionally, because the nucleotide analogs have an unmodified 3' hydroxyls, i.e., as found in "natural" deoxyribose and ribose molecules, the analogs result in "natural" nucleotides when a cleavable blocking group is removed from the base. Other nucleotide analogs can also be used which, for example, include self-eliminating linkers, or nucleotides with modified phosphate groups. In most instances, the blocking group is designed to not leave behind substantial additional molecules, i.e., designed to leave behind "scarless" nucleotides that are recognized as "natural" nucleotides by the enzyme. Thus, at the conclusion of the synthesis, upon removal of the last blocking group, the synthesized polynucleotide is chemically and structurally equivalent to the naturally-occurring polynucleotide with the same sequence. The synthetic polynucleotide can, thus, be incorporated into living systems without concern that the synthesized polynucleotide will interfere with biochemical pathways or metabolism.

The process and analogs of the current invention can be used for the non-templated enzymatic synthesis of useful oligo- and oligodeoxynucleotides especially of long oligonucleotides (<5000 nt). Products can be single strand or partially double strand depending upon the initiator used. The synthesis of long oligonucleotides requires high efficiency incorporation and high efficiency of reversible terminator removal. The initiator bound to the solid support consists of a short, single strand DNA sequence that is either a short piece of the user defined sequence or a universal initiator from which the user defined single strand product is removed.

In one aspect, the disclosed methods employ commercially-available nucleotidyl transferase enzymes, such as terminal deoxynucleotidyl transferase (TdT), to synthesize polynucleotides from nucleotide analogs in a step-by-step fashion. The nucleotide analogs are of the form:

NTP-linker-inhibitor wherein NTP is a nucleotide triphosphate (i.e., a dNTP or an rNTP), the linker is a cleavable linker between the pyridine or pyrimidine of the base, and the inhibitor is a group that prevents the enzyme from incorporating subsequent nucleotides. At each step, a new nucleotide analog is incorporated into the growing polynucleotide chain, whereupon the enzyme is blocked from adding an additional nucleotide by the inhibitor group. Once the enzyme has stopped, the excess nucleotide analogs can be removed from the growing chain, the inhibitor can be cleaved from the NTP, and new nucleotide analogs can be introduced in order to add the next nucleotide to the chain. By repeating the steps sequentially, it is possible to quickly construct nucleotide sequences of a desired length and sequence. Advantages of using nucleotidyl transferases for polynucleotide synthesis include: 1) 3'-extension activity using single strand (ss) initiating primers in a template-independent polymerization, 2) the ability to extend primers in a highly efficient manner resulting in the addition of thousands of nucleotides, and 3) the acceptance of a wide variety of modified and substituted NTPs as efficient substrates. In addition, the invention can make use of an initiator sequence that is a substrate for nucleotidyl transferase. The initiator is attached to a solid support and serves as a binding site for the enzyme. The initiator is preferably a universal initiator for the enzyme, such as a homopolymer sequence and is recyclable on the solid support, the formed oligonucleotide being cleavable from the initiator.

Methods of the invention are well-suited to a variety of applications that currently use synthetic nucleic acids, e.g., phosphoramidite-synthesized DNA oligos. For example, polynucleotides synthesized with the methods of the invention can be used as primers for nucleic acid amplification, hybridization probes for detection of specific markers, and for incorporation into plasmids for genetic engineering. However, because the disclosed methods produce longer synthetic strings of nucleotides, at a faster rate, and in an aqueous environment, the disclosed methods also lend themselves to high-throughput applications, such as screening for expression of genetic variation in cellular assays, as well as synthetic biology. Furthermore, the methods of the invention will provide the functionality needed for next-generation applications, such as using DNA as synthetic read/write memory, or creating macroscopic materials synthesized completely (or partially) from DNA.

The invention and systems described herein provide for synthesis of polynucleotides, including deoxyribonucleic acids (DNA) and ribonucleic acids (RNA). While synthetic pathways for "natural" nucleotides, such as DNA and RNA, are described in the context of the common nucleic acid bases, e.g., adenine (A), guanine (G), cytosine (C), thymine (T), and uracil(U), it is to be understood that the methods of the invention can be applied to so-called "non-natural" nucleotides, including nucleotides incorporating universal bases such as 3-nitropyrrole 2'-deoxynucloside and 5-nitroindole 2'-deoxynucleoside, alpha phosphorothiolate, phosphorothioate nucleotide triphosphates, or purine or pyrimidine conjugates that have other desirable properties, such as fluorescence. Other examples of purine and pyrimidine bases include pyrazolo[3,4-d]pyrimidines, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-propynyl uracil and cytosine, 6-azo uracil, cytosine and thymine, 5-uracil (pseudouracil), 4-thiouracil, 8-halo (e.g., 8-bromo), 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, deazaguanine, 7-deazaguanine, 3-deazaguanine, deazaadenine, 7-deazaadenine, 3-deazaadenine, pyrazolo[3,4-d]pyrimidine, imidazo[1,5-a]1,3,5 triazinones, 9-deazapurines, imidazo[4,5-d]pyrazines, thiazolo[4,5-d]pyrimidines, pyrazin-2-ones, 1,2,4-triazine, pyridazine; and 1,3,5 triazine. In some instances, it may be useful to produce nucleotide sequences having unreactive, but approximately equivalent bases, i.e., bases that do not react with other proteins, i.e., transcriptases, thus allowing the influence of sequence information to be decoupled from the structural effects of the bases.

Analogs

The invention provides nucleotide analogs having the formula NTP-linker-inhibitor for synthesis of polynucleotides in an aqueous environment. With respect to the analogs of the form NTP-linker-inhibitor, NTP can be any nucleotide triphosphate, such as adenosine triphosphate (ATP), guanosine triphosphate (GTP), cytidine triphosphate (CTP), thymidine triphosphate (TTP), uridine triphosphate (UTP), nucleotide triphosphates, deoxyadenosine triphosphate (dATP), deoxyguanosine triphosphate (dGTP), deoxycytidine triphosphate (dCTP), deoxythymidine triphosphate (dTTP), or deoxyuridine triphosphate (dUTP).

The linker can be any molecular moiety that links the inhibitor to the NTP and can be cleaved, e.g., chemically cleaved, electrochemically cleaved, enzymatically cleaved, or photolytically cleaved. For example, the linkers can be cleaved by adjusting the pH of the surrounding environment. The linkers may also be cleaved by an enzyme that is activated at a given temperature, but inactivated at another temperature. In some embodiments, the linkers include disulfide bonds.

The linker can be attached, for example, at the N4 of cytosine, the N3 or O4 of thymine, the N2 or N3 of guanine, and the N6 of adenine, or the N3 or O4 of uracil because attachment at a carbon results in the presence of a residual scar after removal of the polymerase-inhibiting group. The linker is typically on the order of at least about 10 Angstroms long, e.g., at least about 20 Angstroms long, e.g., at least about 25 Angstroms long, thus allowing the inhibitor to be far enough from the pyridine or pyrimidine to allow the enzyme to bind the NTP to the polynucleotide chain via the attached sugar backbone. In some embodiments, the cleavable linkers are self-cyclizing in that they form a ring molecule that is particularly non-reactive toward the growing nucleotide chain.

The nucleotide analogs can include any moiety linked to the NTP that inhibits the coupling of subsequent nucleotides by the enzyme. The inhibitory group can be a charged group, such as a charged amino acid, or the inhibitory group can be a group that becomes charged depending upon the ambient conditions. In some embodiments, the inhibitor may include a moiety that is negatively charged or capable of becoming a negatively charged. In other embodiments, the inhibitor group is positively charged or capable of becoming positively charged. In some other embodiments, the inhibitor is an amino acid or an amino acid analog. The inhibitor may be a peptide of 2 to 20 units of amino acids or analogs, a peptide of 2 to 10 units of amino acids or analogs, a peptide of 3 to 7 units of amino acids or analogs, a peptide of 3 to 5 units of amino acids or analogs. In some embodiments, the inhibitor includes a group selected from the group consisting of Glu, Asp, Arg, His, and Lys, and a combination thereof (e.g., Arg, Arg-Arg, Asp, Asp-Asp, Asp, Glu, Glu-Glu, Asp-Glu-Asp, Asp-Asp-Glu or AspAspAspAsp, etc.). Peptides or groups may be combinations of the same or different amino acids or analogs. The inhibitory group may also include a group that reacts with residues in the active site of the enzyme thus interfering with the coupling of subsequent nucleotides by the enzyme.

Figure 1B:
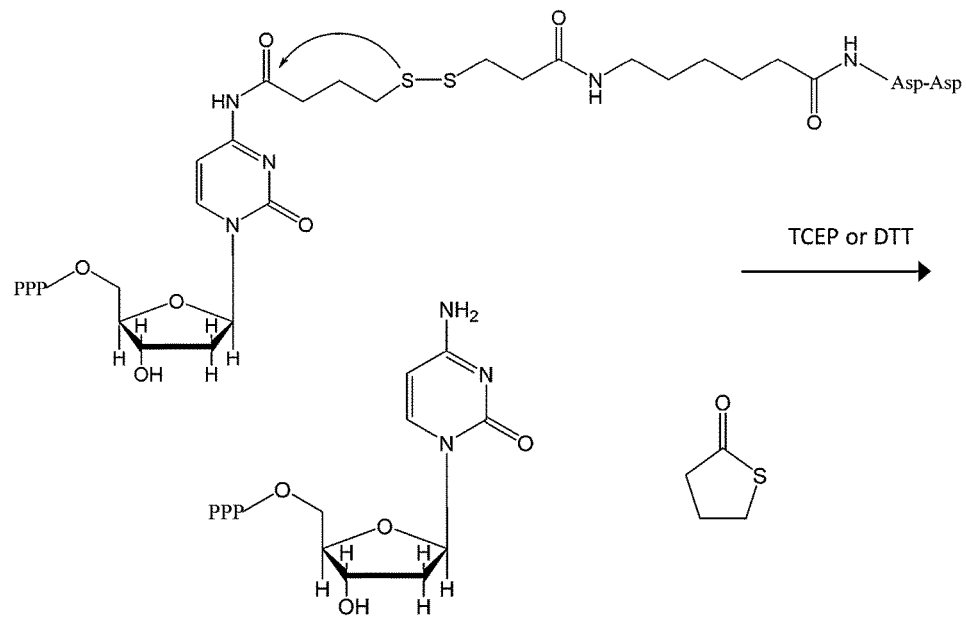
FIG. 1B shows cleavage of the cleavable terminator from a dCTP analog of FIG. 1A to achieve a "natural" dCTP and a cyclic leaving molecule.

An example of a nucleotide analog of the type NTP-linker-inhibitor is shown in FIG. 1A. The analog in FIG. 1A includes an inhibitory (-Asp-Asp-) group linked to the N4 position of dCTP through a disulfide (—S—S—) bond while providing an unblocked, unmodified 3'-OH on the sugar ring. The linker is constructed such that all linker atoms (including the 2nd incorporation-inhibiting moiety) can be removed, thereby allowing the nascent DNA strand to revert to natural nucleotides. As shown in FIG. 1B, an aqueous reducing agent, such as tris(2-carboxyethyl)phosphine (TCEP) or dithiothreitol (DTT), can be used to cleave the —S—S— bond, resulting in the loss of the inhibitor function (deblocking). As shown in FIG. 1B, a self-cyclizing linker can be incorporated, resulting in a cyclic oxidized tetrahydrothiophene leaving group that is easily removed from the reagent solution at the conclusion of nucleotide synthesis.

An exemplary scheme for synthesizing a dCTP analog of FIG. 1A is shown below:

Scheme 1

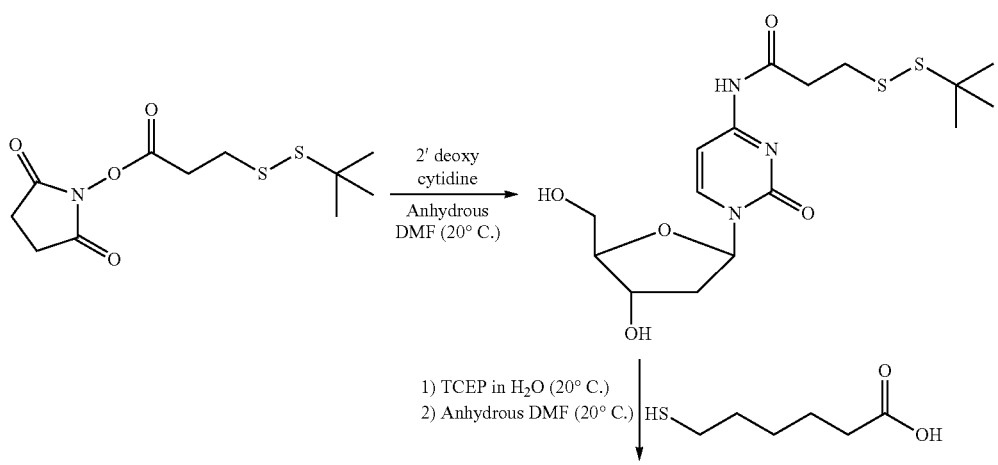

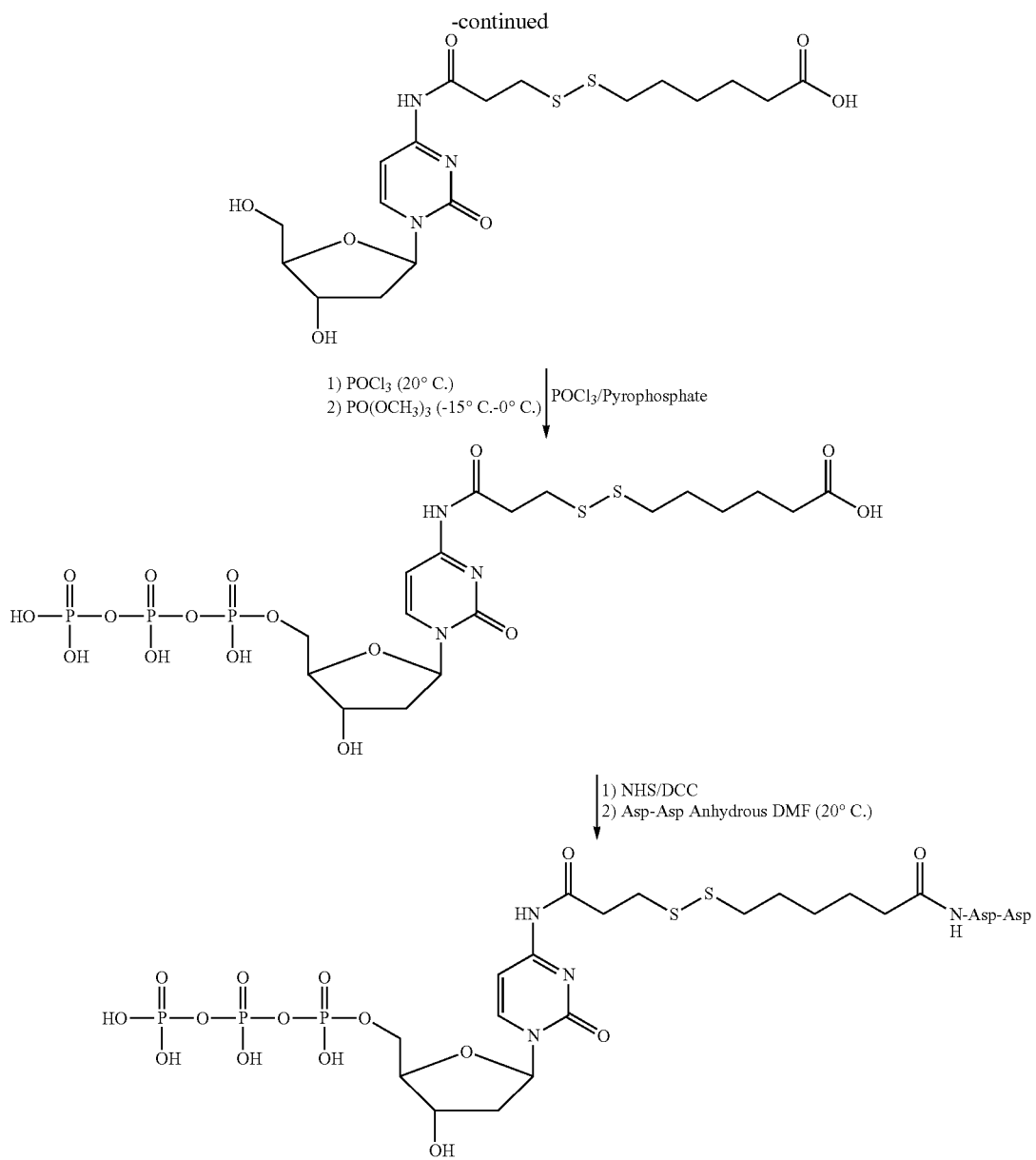

Figure 2A:
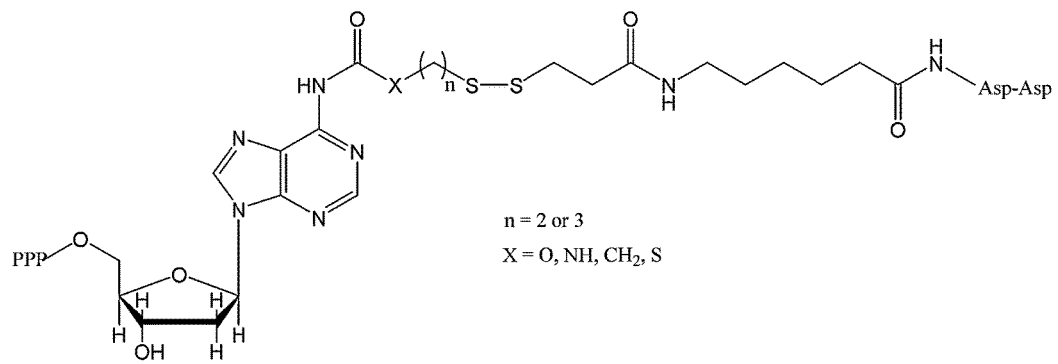
FIG. 2A shows a genus of deoxyadenosine triphosphate (dATP) analogs having a cleavable terminator linked at the N-6 position.
Figure 2B:
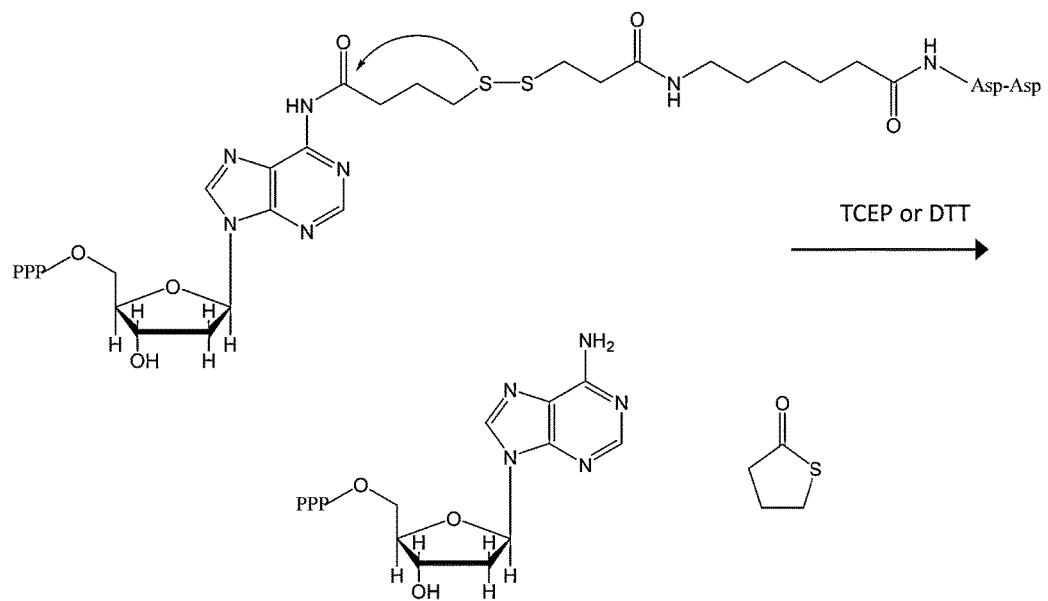
FIG. 2B shows cleavage of the cleavable terminator from a dATP analog of FIG. 2A to achieve a "natural" dATP and a cyclic leaving molecule.
Figure 3A:
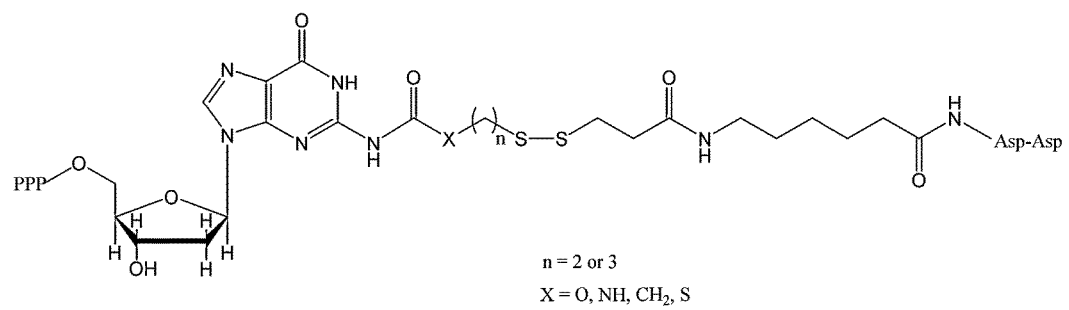
FIG. 3A shows a genus of deoxyguanosine triphosphate (dGTP) analogs having a cleavable terminator linked at the N-2 position.
Figure 3B:
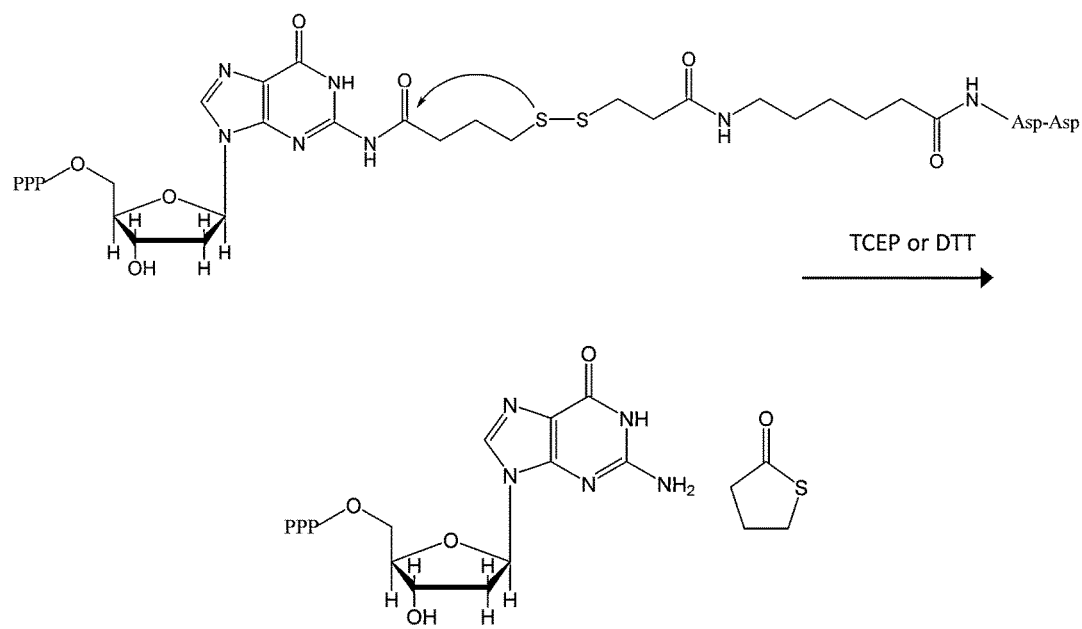
FIG. 3B shows cleavage of the cleavable terminator from a dGTP analog of FIG. 3A to achieve a "natural" dGTP and a cyclic leaving molecule.
Figure 4A:
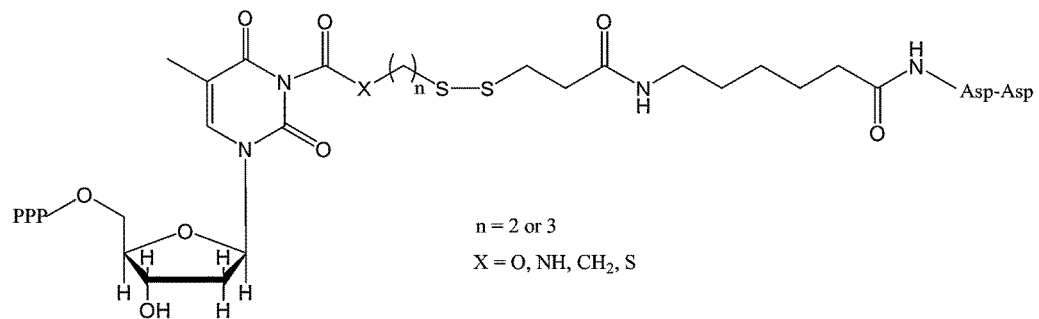
FIG. 4A shows a genus of deoxythymidine triphosphate (dTTP) analogs having a cleavable terminator linked at the N-3 position.
Figure 4B:
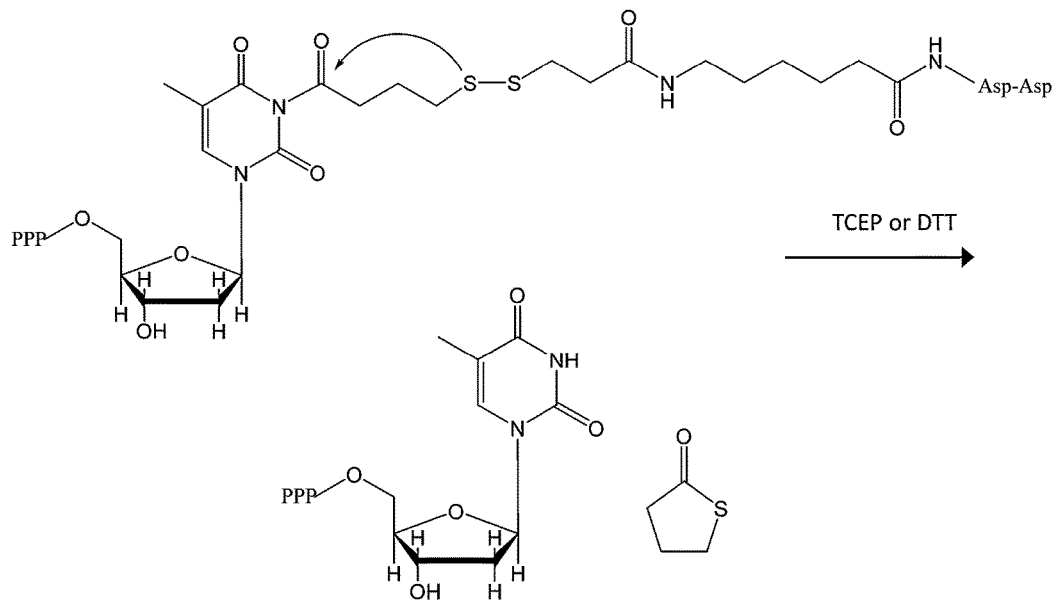
FIG. 4B shows cleavage of the cleavable terminator from a dTTP analog of FIG. 4A to achieve a "natural" dTTP and a cyclic leaving molecule.
Figure 5A:
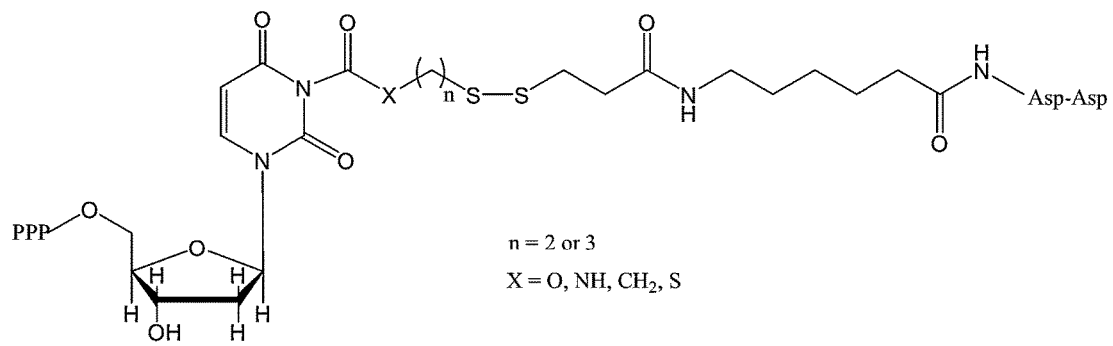
FIG. 5A shows a genus of deoxyuridine triphosphate (dUTP) analogs having a cleavable terminator linked at the N-3 position.
Figure 5B:
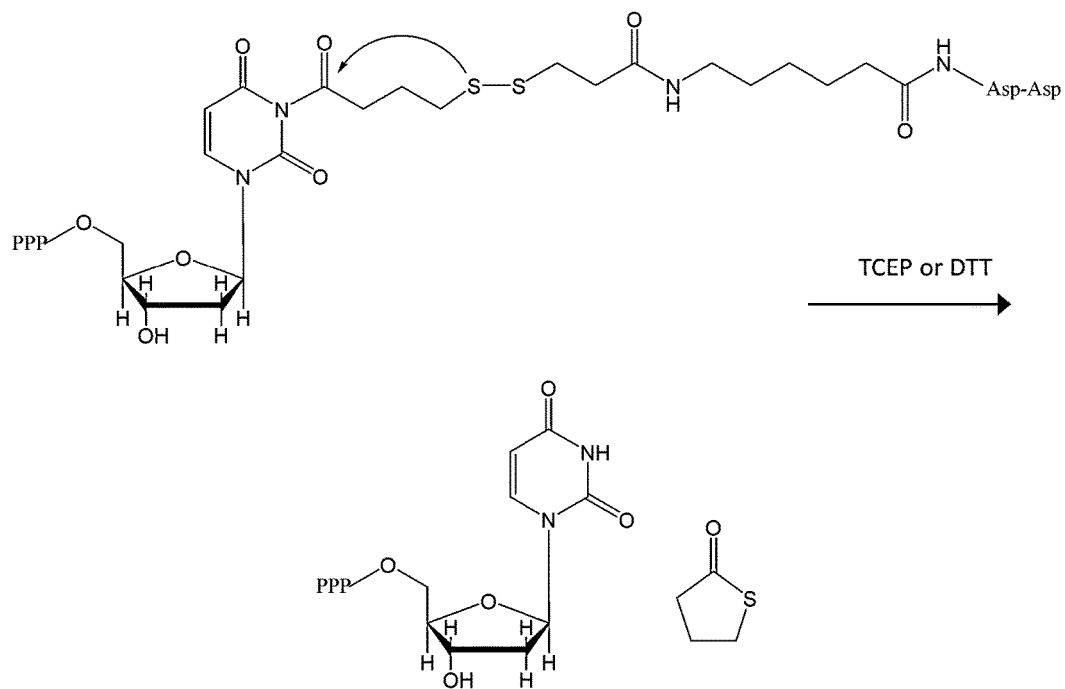
FIG. 5B shows cleavage of the cleavable terminator from a dUTP analog of FIG. 5A to achieve a dUTP and a cyclic leaving molecule.

In a fashion analogous to FIG. 1, nucleotide analogs of the type NTP-linker-inhibitor can also be formed by attaching the linker-inhibitor moiety to the N6 of adenine (FIG. 2), the N2 of guanine (FIG. 3), the N3 of thymine (FIG. 4), or the N3 of uracil (FIG. 5), thereby providing analogs of the "naturally-occurring" dNTPs, as well as a deoxyuracil nucleotide (dUTP). While it is unlikely that there will be wide use of a dUTP, the synthesis is straightforward based upon the chemistry.

The invention is not limited to the linking chemistry of Scheme 1, however, as carbamate, amide, or other self-eliminating linkages could also be employed. For example, nucleotides can also be prepared with Staudinger linkers, as shown in Scheme 2.

Scheme 2

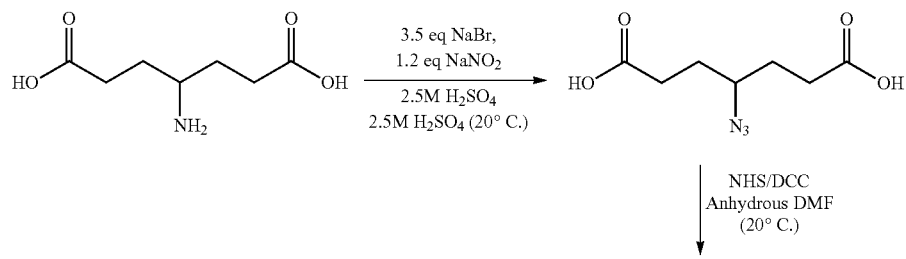

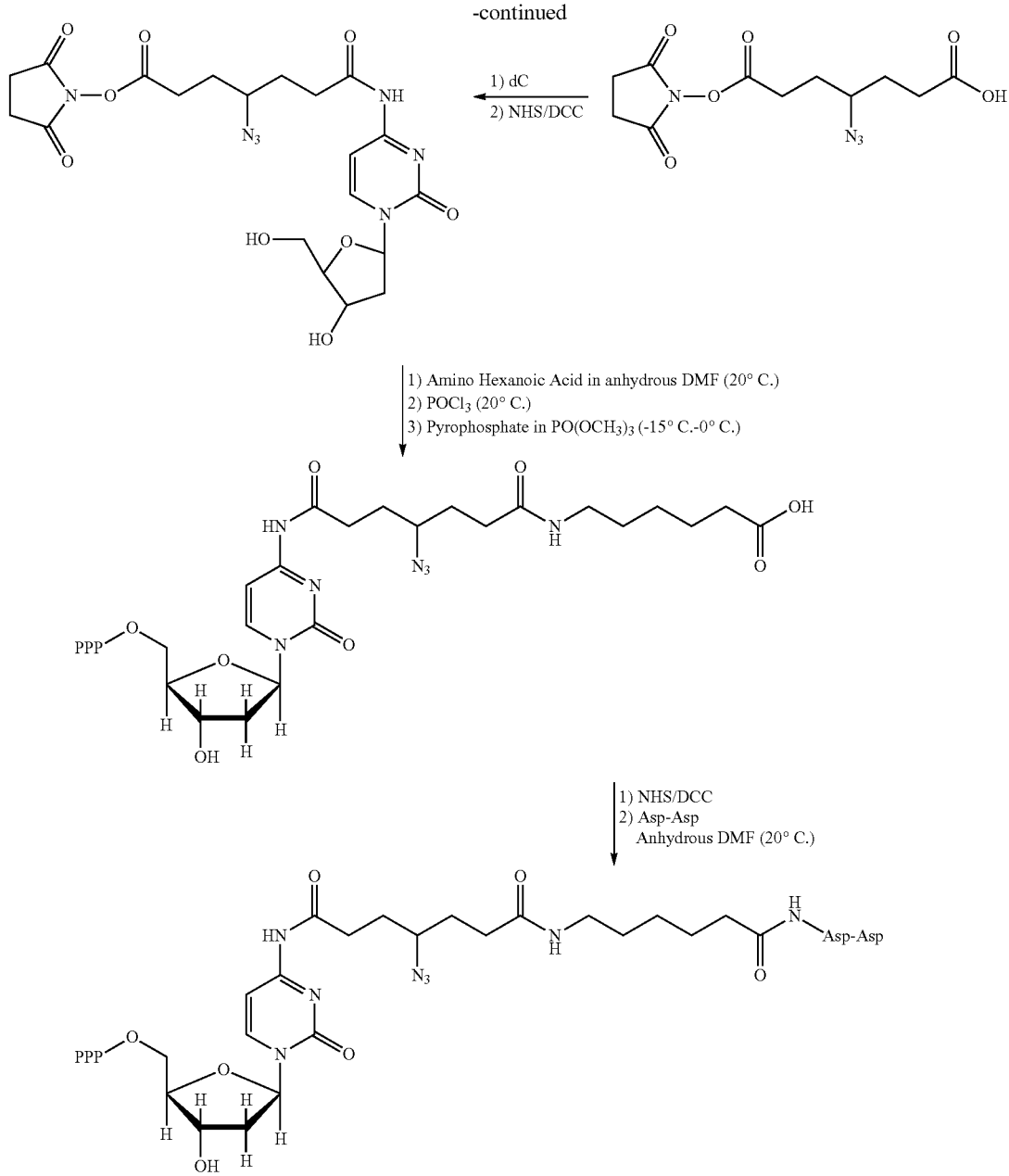

Figure 6:
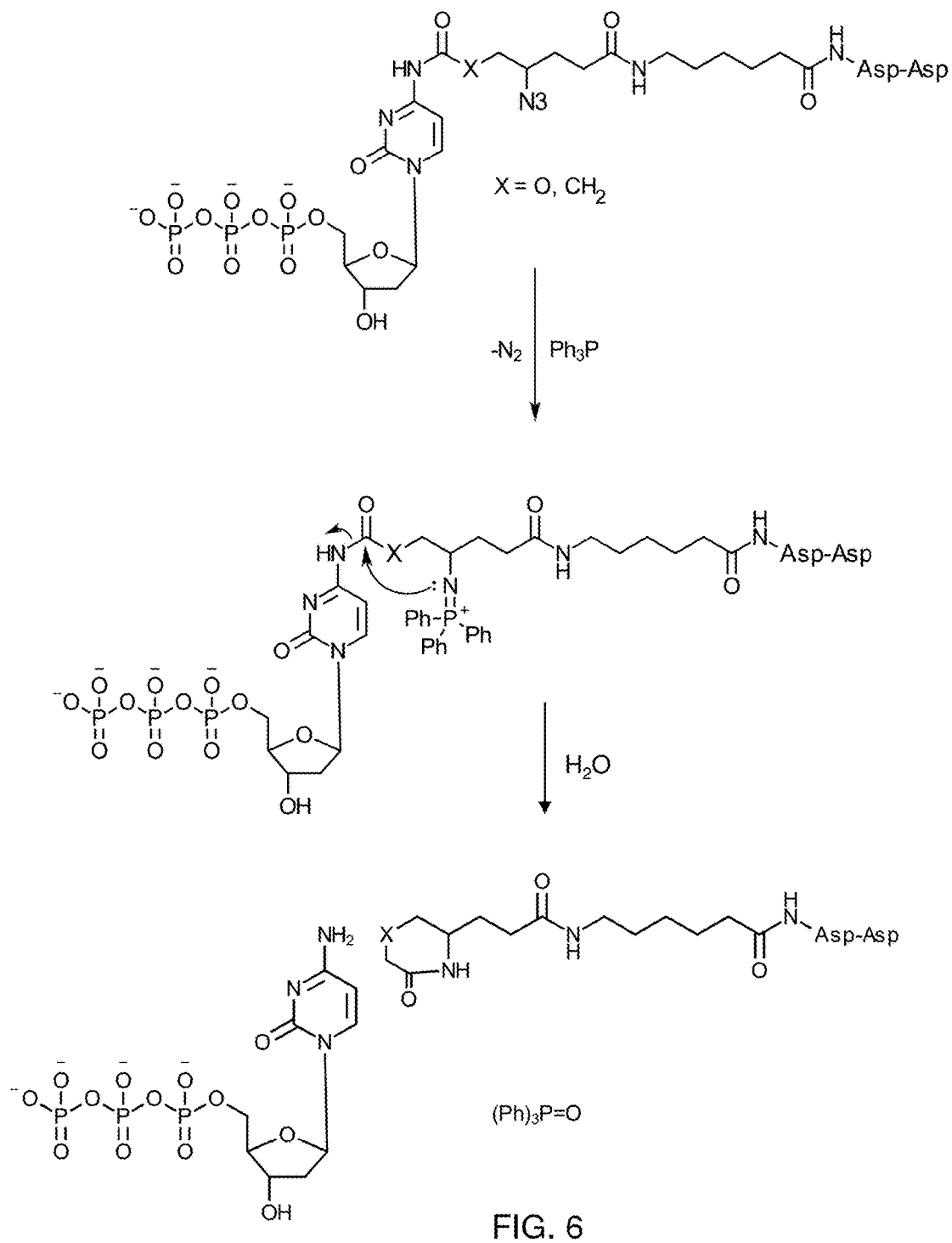
FIG. 6 shows an exemplary deoxycytidine triphosphate (dCTP) analog having a Staudinger linker connecting a blocking Asp-Asp molecule to the N-4 position of the deoxycytidine and subsequent cleavage of the Staudinger linker under aqueous conditions to achieve a dCTP and a leaving group.

A deoxycytidine triphosphate (dCTP) analog created with a Staudinger linker (Scheme 2) to an Asp-Asp blocking group is shown in FIG. 6. As shown in FIG. 6, the Staudinger dCTP analog undergoes cleavage under aqueous conditions with the addition of azide and triphenylphosphine. The Staudinger analog shown in FIG. 6 is also suitable for nucleotide extension using nucleotidyl transferases, such as TdT, as described above and exemplified in FIGS. 1-5. While not shown explicitly in the FIGS., one of skill in the art can use Scheme 2 in conjunction with the suitable reactant to produce other nucleotide analogs having Staudinger linkers as needed for complete de novo nucleotide synthesis. In a fashion analogous to FIG. 6, nucleotide analogs of Scheme 2 can be formed by attaching the Staudinger moiety to the N6 of adenine, the N2 of guanine, the N3 of thymine, or the N3 of uracil, thereby providing analogs of the "naturally-occurring" dNTPs, as well as a deoxyuracil nucleotide (dUTP).

Figure 12:
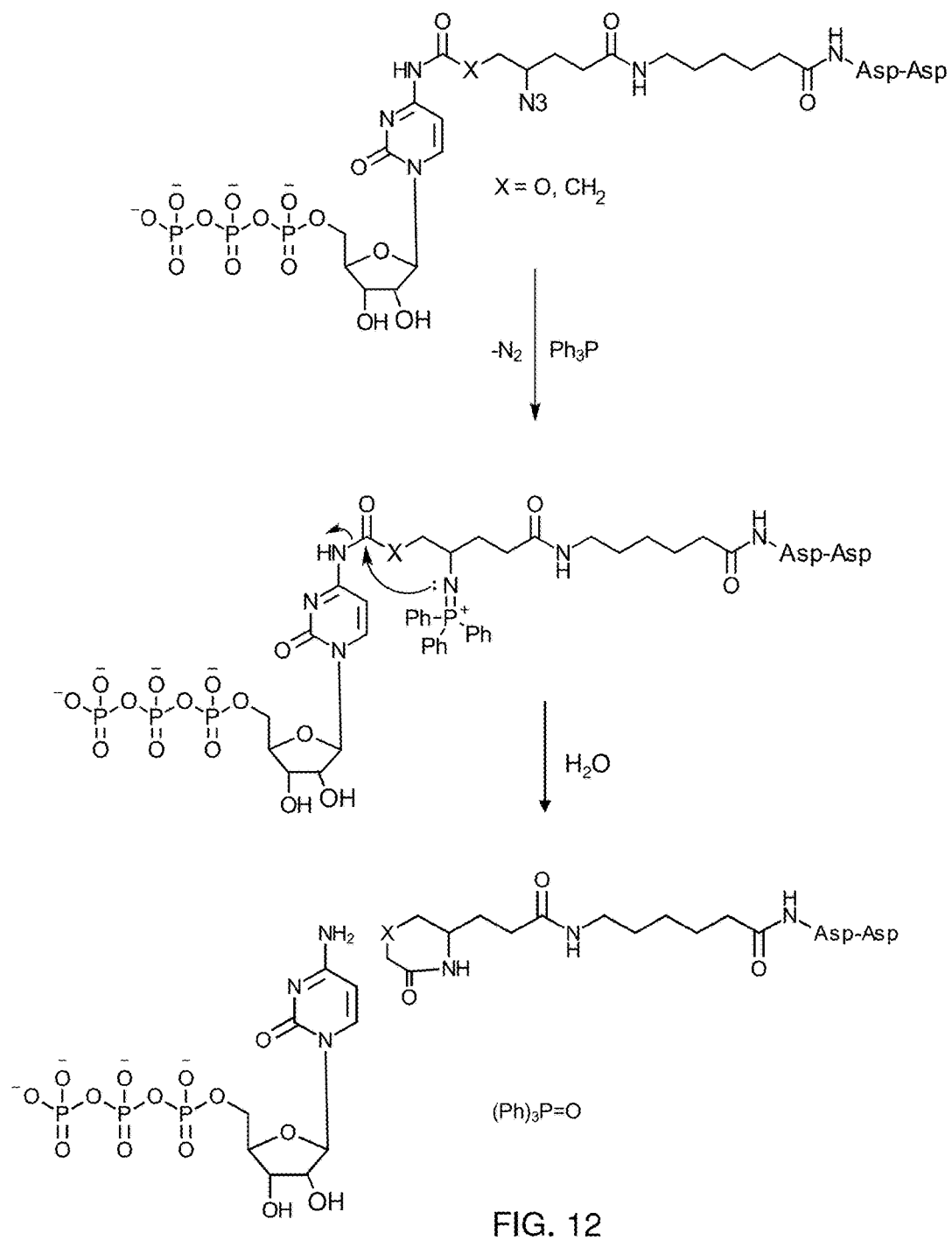
FIG. 12 shows an exemplary cytidine triphosphate (rCTP) analog having a Staudinger linker connecting a blocking Asp-Asp molecule to the N-4 position of the cytidine and subsequent cleavage of the Staudinger linker under aqueous conditions to achieve a rCTP and a leaving group.

The methodologies of Scheme 1 can be used to produce corresponding ribonucleotide analogs, e.g., as shown in FIGS. 7-10, by starting with the appropriate ribonucleotide reactants. Ribonucleotide analogs comprising the Staudinger linker can also be created using Scheme 2 in order to form the needed ribonucleotide analogs, including, e.g., CTP analogs, as shown in FIG. 12. Furthermore, all of the ribonucleotide analogs, i.e., C, A, T, G, U, can be formed using a reaction similar to Scheme 2.

Enzymes

The methods of the invention employ nucleotidyl transferases to assemble the nucleotide analogs into polynucleotides. Nucleotidyl transferases include several families of related transferase and polymerase enzymes. Some nucleotidyl transferases polymerize deoxyribonucleotides more efficiently than ribonucleotides, some nucleotidyl transferases polymerize ribonucleotides more efficiently than deoxyribonucleotides, and some nucleotidyl transferases polymerize ribonucleotides and deoxyribonucleotides at approximately the same rate.

Of particular import to the invention, transferases having polymerase activity, such as terminal deoxynucleotidyl transferase (TdT), are capable of catalyzing the addition of deoxyribonucleotides to the 3' end of a nucleotide chain, thereby increasing chain length in DNA nucleotides. TdT will only catalyze the addition of 1-2 ribonucleotides to the growing end of a DNA strand which could be useful in the construction of site specific DNA-RNA chimeric polynucleotides. In particular, calf thymus TdT, sourced from engineered E. coli, is suitable for use with the invention and available from commercial sources such as Thermo Scientific (Pittsburgh, Pa.). The amino acid sequence corresponding to calf TdT is listed in Table 1 as SEQ ID NO. 1.

TABLE 1

Amino Acid Sequence of Bovine TdT

SEQ ID NO. 1:
MAQQRQHQRL PMDPLCTASS GPRKKRPRQV GASMASPPHD

IKFQNLVLFI LEKKMGTTRR NFLMELARRK GFRVENELSD

SVTHIVAENN SGSEVLEWLQ VQNIRASSQL ELLDVSWLIE

SMGAGKPVEI TGKHQLVVRT DYSATPNPGF QKTPPLAVKK

ISQYACQRKT TLNNYNHIFT DAFEILAENS EFKENEVSYV

TFMRAASVLK SLPFTIISMK DTEGIPCLGD KVKCIIEEII

EDGESSEVKA VLNDERYQSF KLFTSVFGVG LKTSEKWFRM

GFRSLSKIMS DKTLKFTKMQ KAGFLYYEDL VSCVTRAEAE

AVGVLVKEAV WAFLPDAFVT MTGGFRRGKK IGHDVDFLIT

SPGSAEDEEQ LLPKVINLWE KKGLLLYYDL VESTFEKFKL

PSRQVDTLDH FQKCFLILKL HHQRVDSSKS NQQEGKTWKA

IRVDLVMCPY ENRAFALLGW TGSRQFERDI RRYATHERKM

MLDNHALYDK TKRVFLKAES EEEIFAHLGL DYIEPWERNA

The nucleotide sequence corresponding to calf TdT is listed in Table 2 as SEQ ID NO. 2.

TABLE 2

Nucleic Acid Sequence of Bovine TdT

SEQ ID NO. 2:
ctcttctgga gataccactt gatggcacag cagaggcagc atcagcgtct tcccatggat ccgctgtgca cagcctcctc aggccctcgg aagaagagac ccaggcaggt gggtgcctca atggcctccc ctcctcatga catcaagttt caaaatttgg tcctcttcat tttggagaag aaaatgggaa ccaccgcag aaacttcctc atggagctgg ctcgaaggaa aggtttcagg gttgaaaatg agctcagtga ttctgtcacc cacattgtag cagaaaacaa ctctggttca gaggttctcg agtggcttca TABLE 2-continued Nucleic Acid Sequence of Bovine TdT ggtacagaac ataagagcca gctcgcagct agaactcctt gatgtctcct ggctgatcga agtatggga gcaggaaaac cagtggagat tacaggaaaa caccagcttg ttgtgagaac agactattca gctacccaa acccaggctt ccagaagact ccaccacttg ctgtaaaaaa gatctcccag tacgcgtgtc aaagaaaaac cactttgaac aactataacc acatattcac ggatgccttt gagatactgg ctgaaaattc tgagtttaaa gaaaatgaag tctcttatgt gacatttatg agagcagctt ctgtacttaa atctctgcca ttcacaatca tcagtatgaa ggatacagaa ggaattccct gcctggggga caaggtgaag tgtatcatag aggaaattat tgaagatgga gaaagttctg aagttaaagc tgtgttaaat gatgaacgat atcagtcctt caaactcttt acttctgttt ttggagtggg actgaagaca tctgagaaat ggttcaggat ggggttcaga tctctgagta aaataatgtc agacaaaacc ctgaaattca caaaaatgca gaaagcagga tttctctatt atgaagacct tgtcagctgc gtgaccaggg ccgaagcaga ggcggttggc gtgctggtta aagaggctgt gtgggcattt ctgccggatg cctttgtcac catgacagga ggattccgca ggggtaagaa gattgggcat gatgtagatt ttttaattac cagcccagga tcagcagagg atgaagagca acttttgcct aaagtgataa acttatggga aaaaaaggga ttacttttat attatgacct tgtggagtca acatttgaaa agttcaagtt gccaagcagg caggtggata ctttagatca ttttcaaaaa tgctttctga ttttaaaatt gcaccatcag agagtagaca gtagcaagtc caaccagcag gaaggaaaga cctggaaggc catccgtgtg gacctggtta tgtgcccta cgagaaccgt gcctttgccc tgctaggctg gactggctcc cggcagtttg agagagacat ccggcgctat gccacacacg agcggaagat gatgctggat aaccacgctt tatatgacaa gaccaagagg gtatttctca aagcggaaag tgaagaagaa atctttgcac atctgggatt ggactacatt gaaccatggg aaagaaatgc ttaggagaaa gctgtcaact tttttctttt ctgttctttt tttcaggtta gacaaattat gcttcatatt ataatgaaag atgccttagt caagtttggg attctttaca ttttaccaag atgtagattg cttctagaaa taagtagttt tggaaacgtg atcaggcacc ccctgggtta tgctctggca agccatttgc aggactgatg tgtagaactc gcaatgcatt ttccatagaa acagtgttgg aattggtggc tcatttccag ggaagttcat caaagcccac tttgcccaca TABLE 2-continued Nucleic Acid Sequence of Bovine TdT gtgtagctga aatactgtat acttgccaat aaaaatagga aac While commercially-available TdT is suitable for use with the methods of the invention, modified TdT, e.g., having an amino acid sequence at least 95% in common with SEQ ID NO. 1, e.g., having an amino acid sequence at least 98% in common with SEQ ID NO. 1, e.g., having an amino acid sequence at least 99% in common with SEQ ID NO. 1, may be used with the methods of the invention. An organism that expresses a suitable nucleotidyl transferase may comprise a nucleic acid sequence at least 95% in common with SEQ ID NO. 2, e.g., at least 98% in common with SEQ ID NO. 2, e.g., at least 99% in common with SEQ ID NO. 2. In some instances, a modified TdT will result in more efficient generation of polynucleotides, or allow better control of chain length. Other modifications to the TdT may change the release characteristics of the enzyme, thereby reducing the need for aqueous reducing agents such as TCEP or DTT.

For the synthesis of RNA polynucleotides, a nucleotidyl transferase like E. coli poly(A) polymerase can be used to catalyze the addition of ribonucleotides to the 3' end of a ribonucleotide initiator. In other embodiments, E. coli poly (U) polymerase may be more suitable for use with the methods of the invention. Both E. coli poly(A) polymerase and E. coli poly(U) polymerase are available from New England Biolabs (Ipswich, Mass.). The amino acid and nucleotide sequences for E. coli Poly(A) polymerase and E. coli Poly(U) polymerase are reproduced below. Modified E. coli Poly(A) polymerase or E. coli Poly(U) polymerase may be suitable for use with the methods of the invention. For example, an enzyme, having an amino acid sequence at least 95% in common with SEQ ID NO. 3, e.g., having an amino acid sequence at least 98% in common with SEQ ID NO. 3, e.g., having an amino acid sequence at least 99% in common with SEQ ID NO. 3, may be used with the methods of the invention. An organism that expresses a suitable enzyme may comprise a nucleic acid sequence at least 95% in common with SEQ ID NO. 4, e.g., at least 98% in common with SEQ ID NO. 4, e.g., at least 99% in common with SEQ ID NO. 4. Alternatively, an enzyme having an amino acid sequence at least 95% in common with SEQ ID NO. 5, e.g., having an amino acid sequence at least 98% in common with SEQ ID NO. 5, e.g., having an amino acid sequence at least 99% in common with SEQ ID NO. 5, may be used with the methods of the invention. An organism that expresses a suitable enzyme may comprise a nucleic acid sequence at least 95% in common with SEQ ID NO. 6, e.g., at least 98% in common with SEQ ID NO. 6, e.g., at least 99% in common with SEQ ID NO. 6.

TABLE 3

Amino Acid Sequence of E. coli Poly(A) polymerase

SEQ ID NO. 3:
MFTRVANFCR KVLSREESEA EQAVARPQVT VIPREQHAIS

RKDISENALK VMYRLNKAGY EAWLVGGGVR DLLLGKKPKD

FDVTTNATPE QVRKLFRNCR LVGRRFRLAH VMFGPEIIEV

ATFRGHHEGN VSDRTTSQRG QNGMLLRDNI FGSIEEDAQR

TABLE 3-continued

Amino Acid Sequence of E. coli Poly(A) polymerase

RDFTINSLYY SVADFTVRDY VGGMKDLKDG VIRLIGNPET

RYREDPVRML RAVRFAAKLG MRISPETAEP IPRLATLLND

IPPARLFEES LKLLQAGYGY ETYKLLCEYH LFQPLFPTIT

RYFTENGDSP MERIIEQVLK NTDTRIHNDM RVNPAFLFAA

MFWYPLLETA QKIAQESGLT YHDAFALAMN DVLDEACRSL

AIPKRLTTLT RDIWQLQLRM SRRQGKRAWK LLEHPKFRAA

YDLLALRAEV ERNAELQRLV KWWGEFQVSA PPDQKGMLNE

LDEEPSPRRR TRRPRKRAPR REGTA

The nucleotide sequence corresponding to E. coli poly(A) polymerase is listed in Table 4 as SEQ ID NO. 4.

TABLE 4

Nucleotide Sequence of E. coli Poly(A) polymerase

SEQ ID NO. 4:
attttacccc gagtcgctaa tttttgccgc aaggtgctaa gccgcgagga aagcgaggct gaacaggcag tcgcccgtcc acaggtgacg gtgatcccgc gtgagcagca tgctatttcc cgcaaagata tcagtgaaaa tgccctgaag gtaatgtaca ggctcaataa agcgggatac gaagcctggc tggttggcgg cggcgtgcgc gacctgttac ttggcaaaaa gccgaaagat tttgacgtaa ccactaacgc cacgcctgag caggtgcgca aactgttccg taactgccgc ctggtgggtc gccgtttccg tctggctcat gtaatgtttg gcccggagat tatcgaagtt gcgaccttcc gtggacacca cgaaggtaac gtcagcgacc gcacgacctc ccaacgcggg caaaacggca tgttgctgcg cgacaacatt ttcggctcca tcgaagaaga cgcccagcgc cgcgatttca ctatcaacag cctgtattac agcgtagcgg attttaccgt ccgtgattac gttggcggca tgaaggatct gaaggacggc gttatccgtc tgattggtaa cccggaaacg cgctaccgtg aagatccggt acgtatgctg cgcgcggtac gttttgccgc caaattgggt atgcgcatca gcccggaaac cgcagaaccg atccctcgcc tcgctaccct gctgaacgat atcccaccgg cacgcctgtt tgaagaatcg cttaaactgc tacaagcggg ctacggttac gaaacctata gctgttgtg tgaatatcat ctgttccagc cgctgttccc gaccattacc cgctacttca cggaaatgg cgacagcccg atggagcgga tcattgaaca ggtgctgaag aataccgata cgcgtatcca taacgatatg cgcgtgaacc cggcgttcct gtttgccgcc atgttctggt acccactgct ggagacggca cagaagatcg cccaggaaag cggcctgacc tatcacgacg ctttcgcgct TABLE 4-continued Nucleotide Sequence of E. coli Poly(A) polymerase ggcgatgaac gacgtgctgg acgaagcctg ccgttcactg gcaatcccga aacgtctgac gacattaacc cgcgatatct ggcagttgca gttgcgtatg tcccgtcgtc agggtaaacg cgcatggaaa ctgctggagc atcctaagtt ccgtgcggct tatgacctgt tggccttgcg agctgaagtt gagcgtaacg ctgaactgca gcgtctggtg aaatggtggg gtgagttcca ggtttccgcg ccaccagacc aaaaagggat gctcaacgag ctggatgaag aaccgtcacc gcgtcgtcgt actcgtcgtc cacgcaaacg cgcaccacgt cgtgagggta ccgcatga

TABLE 5

Amino Acid Sequence of E. coli Poly(U) polymerase

SEQ ID NO. 5:
GSHMSYQKVP NSHKEFTKFC YEVYNEIKIS DKEFKEKRAA

LDTLRLCLKR ISPDAELVAF GSLESGLALK NSDMDLCVLM

DSRVQSDTIA LQFYEELIAE GFEGKFLQRA RIPIIKLTSD

TKNGFGASFQ CDIGFNNRLA IHNTLLLSSY TKLDARLKPM

VLLVKHWAKR KQINSPYFGT LSSYGYVLMV LYYLIHVIKP

PVFPNLLLSP LKQEKIVDGF DVGFDDKLED IPPSQNYSSL

GSLLHGFFRF YAYKFEPREK VVTFRRPDGY LTKQEKGWTS

ATEHTGSADQ IIKDRYILAI EDPFEISHNV GRTVSSSGLY

RIRGEFMAAS RLLNSRSYPI PYDSLFEEA

The nucleotide sequence corresponding to *E. coli* poly(U) polymerase is listed in Table 6 as SEQ ID NO. 6.

TABLE 6

Nucleotide Sequence of E. coli Poly(A) polymerase

SEQ ID NO. 6:
ggcagccata tgagctatca gaaagtgccg aacagccata aagaatttac caaattttgc tatgaagtgt ataacgaaat taaaattagc gataaagaat ttaaagaaaa acgcgcggcg ctggataccc tgcgcctgtg cctgaaacgc attagcccgg atgcggaact ggtggcgttt ggcagcctgg aaagcggcct ggcgctgaaa aacagcgata tggatctgtg cgtgctgatg gatagccgcg tgcagagcga taccattgcg ctgcagtttt atgaagaact gattgcggaa ggctttgaag gcaaatttct gcagcgcgcg cgcattccga ttattaaact gaccagcgat accaaaaacg gctttggcgc gagctttcag tgcgatattg gctttaacaa ccgcctggcg attcataaca ccctgctgct gagcagctat accaaactgg atgcgcgcct gaaaccgatg gtgctgctgg tgaaacattg ggcgaaacgc aaacagatta TABLE 6-continued Nucleotide Sequence of E. coli Poly(A) polymerase acagcccgta ttttggcacc ctgagcagct atggctatgt gctgatggtg ctgtattatc tgattcatgt gattaaaccg ccggtgtttc cgaacctgct gctgagcccg ctgaaacagg aaaaaattgt ggatggcttt gatgtgggct ttgatgataa actggaagat attccgccga gccagaacta tagcagcctg ggcagcctgc tgcatggctt ttttcgcttt tatgcgtata aatttgaacc gcgcgaaaaa gtggtgacct ttcgccgccc ggatggctat ctgaccaaac aggaaaaagg ctggaccagc gcgaccgaac ataccggcag cgcggatcag attattaaag atcgctatat tctggcgatt gaagatccgt ttgaaattag ccataacgtg ggccgcaccg tgagcagcag cggcctgtat cgcattcgcg gcgaatttat ggcggcgagc cgcctgctga acagccgcag ctatccgatt ccgtatgata gcctgtttga agaagcg As discussed above, the inhibitor coupled to the nucleotide analog will cause the transferase, e.g., TdT, to not release from the polynucleotide or prevent other analogs from being incorporated into the growing chain. A charged moiety results in better inhibition, however, research suggests that the specific chemical nature of the inhibitor is not particularly important. For example, both phosphates and acidic peptides can be used to inhibit enzymatic activity. See, e.g., Bowers et al., *Nature Methods*, vol. 6, (2009) p. 593-95, and U.S. Pat. No. 8,071,755, both of which are incorporated herein by reference in their entireties. In some embodiments, the inhibitor will include single amino acids or dipeptides, like -(Asp)$_2$, however the size and charge on the moiety can be adjusted, as needed, based upon experimentally determined rates of first nucleotide incorporation and second nucleotide incorporation. That is, other embodiments may use more or different charged amino acids or other biocompatible charged molecule.

Other methods of nucleotide synthesis may be used to build de novo oligonucleotides in a template independent fashion using nucleotidyl transferases or modified nucleotidyl transferases. In one embodiment, the polymerase/transferase enzymes can be modified so that they cease nucleotide addition when they encounter a modification to the phosphate of a 3'-unmodified dNTP analog. This scheme would require a deblocking reagent/reaction that modifies the phosphate end of the nucleotide analog, which frees up the nascent strand for subsequent nucleotide incorporation. Preferred embodiments of this approach would use nucleotide analogs modified only at the phosphates (alpha, beta or gamma) although modifications of the purine/pyrimidine base of the nucleotide are allowed.

Another embodiment for using non-template dependent polymerase/transferase enzymes would be to using protein engineering or protein evolution to modify the enzyme to remain tightly bound and inactive to the nascent strand after each single nucleotide incorporation, thus preventing any subsequent incorporation until such time as the polymerase/transferase is released from the strand by use of a releasing reagent/condition. Such modifications would be selected to allow the use of natural unmodified dNTPs instead of reversible terminator dNTPs. Releasing reagents could be high salt buffers, denaturants, etc. Releasing conditions could be high temperature, agitation, etc. For instance, mutations to the Loop1 and SD1 regions of TdT have been shown to dramatically alter the activity from a template-independent activity to more of a template dependent activity. Specific mutations of interest include but are not limited to $\Delta_3$384/391/392, del loop1 (386→398), D339A, F401A, and Q402K403C404→E402R403S404. Other means of accomplishing the goal of a post-incorporation tight binding TdT enzyme could include mutations to the residues responsible for binding the three phosphates of the initiator strand including but not limited to K261, R432, and R454.

Another embodiment for using non-template dependent polymerase/transferase enzymes would be to use protein engineering or protein evolution to modify the enzyme to accept 3-blocked reversible terminators with high efficiency. Most naturally occurring polymerase/transferase enzymes will not incorporate 3'-blocked reversible terminators due to steric constraints in the active site of the enzyme. Modifying either single or several aa residues in the active site of the enzyme can allow the highly efficient incorporation of 3'-blocked reversible terminators into a support bound initiator in a process completely analogous to that described above. After incorporation, the 3'-reversible terminator is removed with a deblocking reagent/condition thus generating a completely natural (scarless) single strand molecule ready for subsequent controlled extension reactions. There are few residues close to the 3'-OH of the incoming dNTP which explains the propensity of TdT for incorporating ribonucleotide triphosphates as readily as deoxyribonucleotide triphosphates; residues including but not limited to those between β1 and β2 especially R334, Loop1, and those between α13 and α14, especially R454, are likely targets for mutagenesis to accommodate the bulk of 3'-reversible terminator groups and allow their efficient incorporation. Another embodiment for using template-dependent polymerases would be to use the either 3'blocked or 3'unblocked dNTP analogs with a plurality of primer-template pairs attached to a solid support.

Another embodiment for using non-template dependent polymerase/transferase enzymes can use protein engineering or protein evolution to modify the enzyme to optimize the use of each of the four different nucleotides or even different modified nucleotide analogs in an analog specific manner. Nucleotide specific or nucleotide analog specific enzyme variants could be engineered to possess desirable biochemical attributes like reduced $K_m$ or enhanced addition rate which would further reduce the cost of the synthesis of desired polynucleotides.

Solid State Synthesis

Figure 7A:
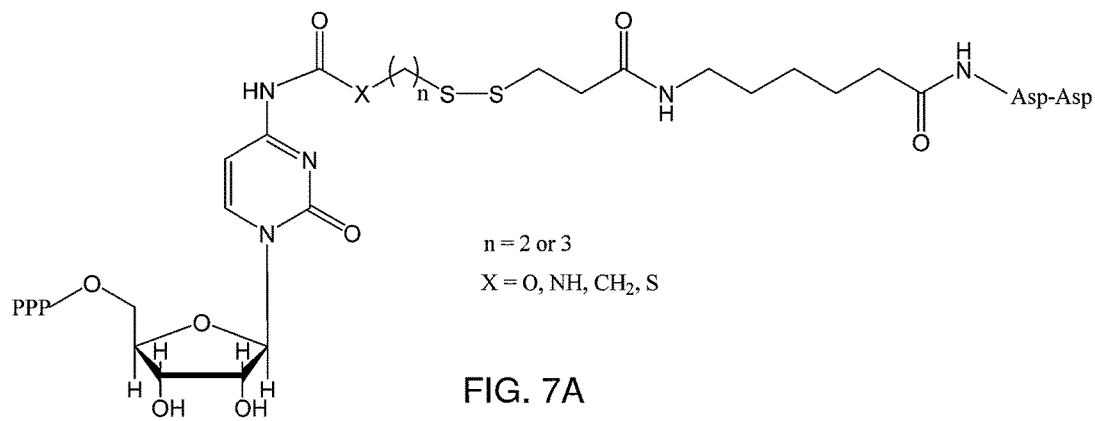
FIG. 7A shows a genus of cytidine triphosphate (rCTP) analogs having a cleavable terminator linked at the N-4 position.
Figure 7B:
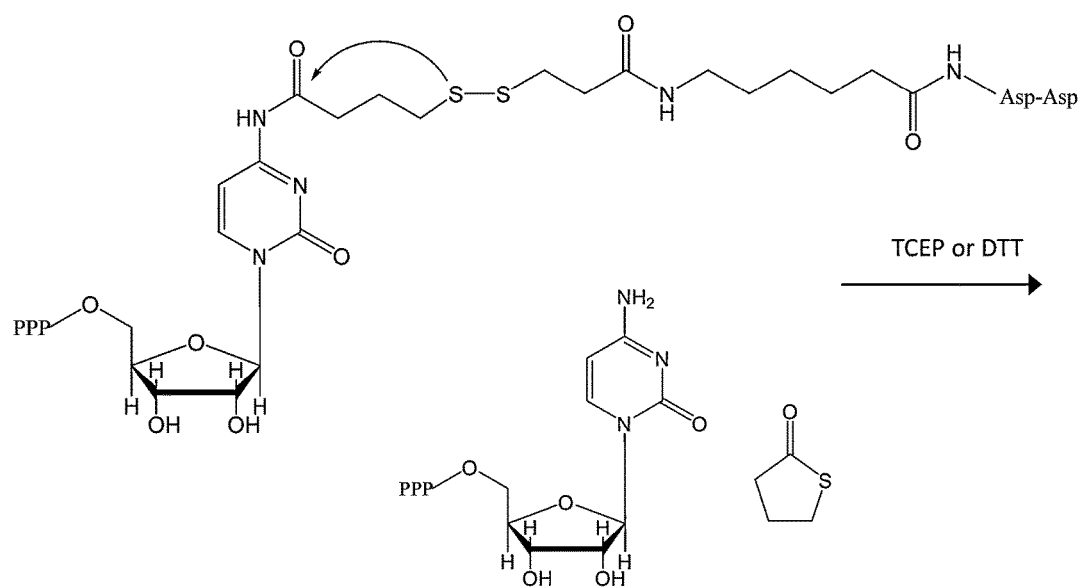
FIG. 7B shows cleavage of the cleavable terminator from a rCTP analog of FIG. 7A to achieve a "natural" rCTP and a cyclic leaving molecule.
Figure 8A:
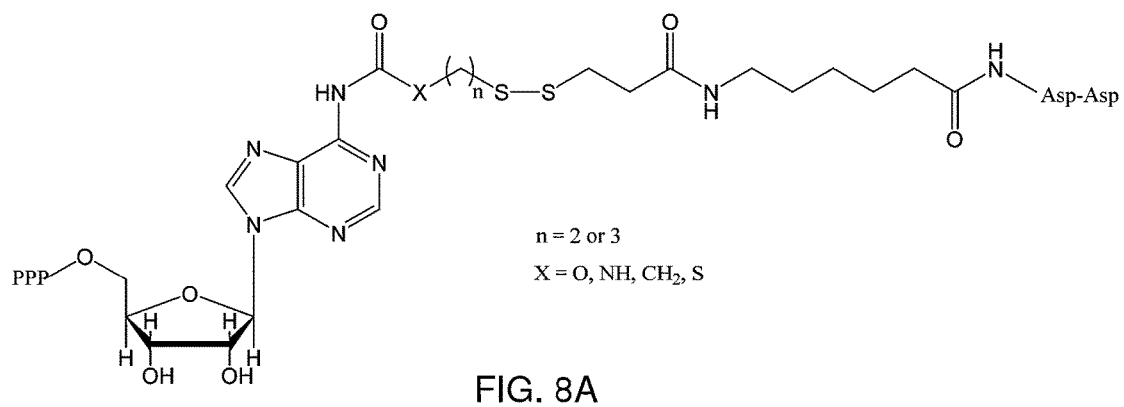
FIG. 8A shows a genus of adenosine triphosphate (rATP) analogs having a cleavable terminator linked at the N-6 position.
Figure 8B:
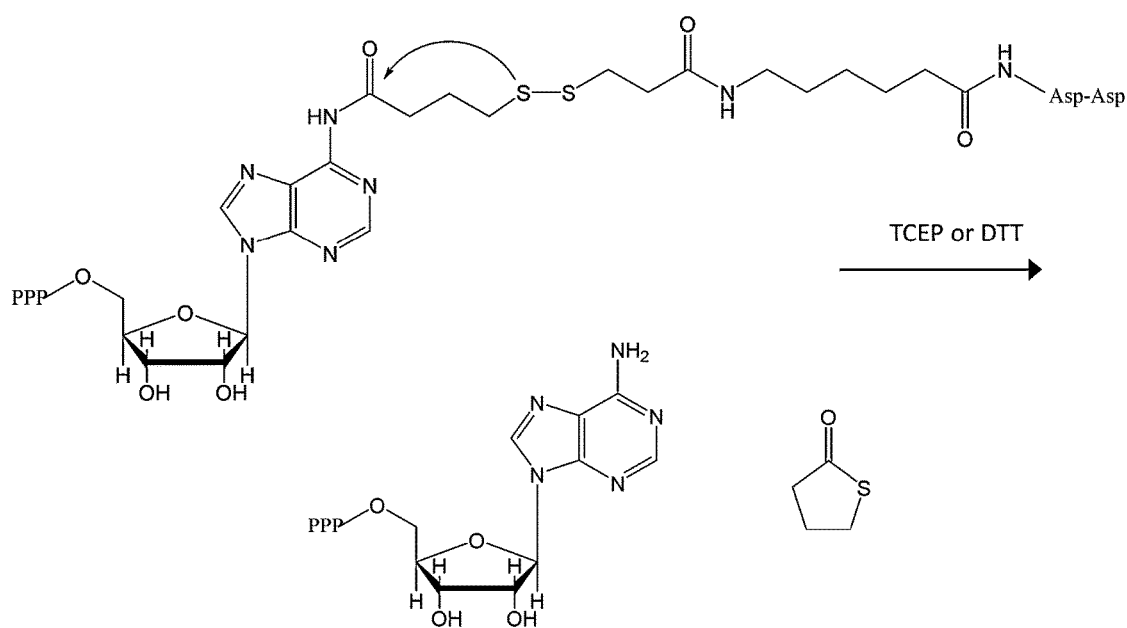
FIG. 8B shows cleavage of the cleavable terminator from an rATP analog of FIG. 8A to achieve a "natural" rATP and a cyclic leaving molecule.
Figure 9A:
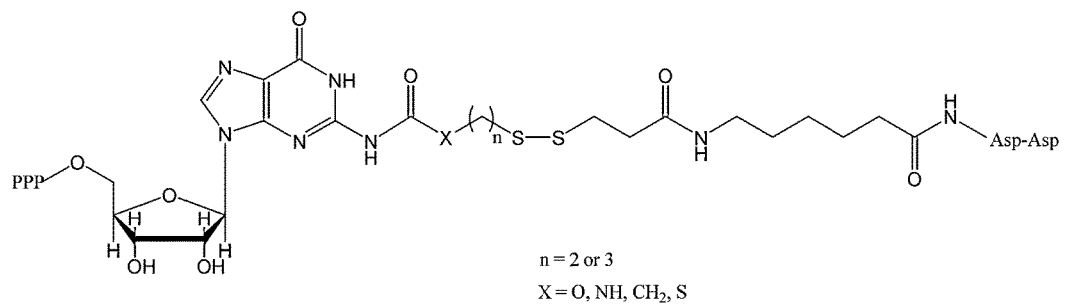
FIG. 9A shows n genus of guanosine triphosphate (rGTP) analogs having a cleavable terminator linked at the N-2 position.
Figure 9B:
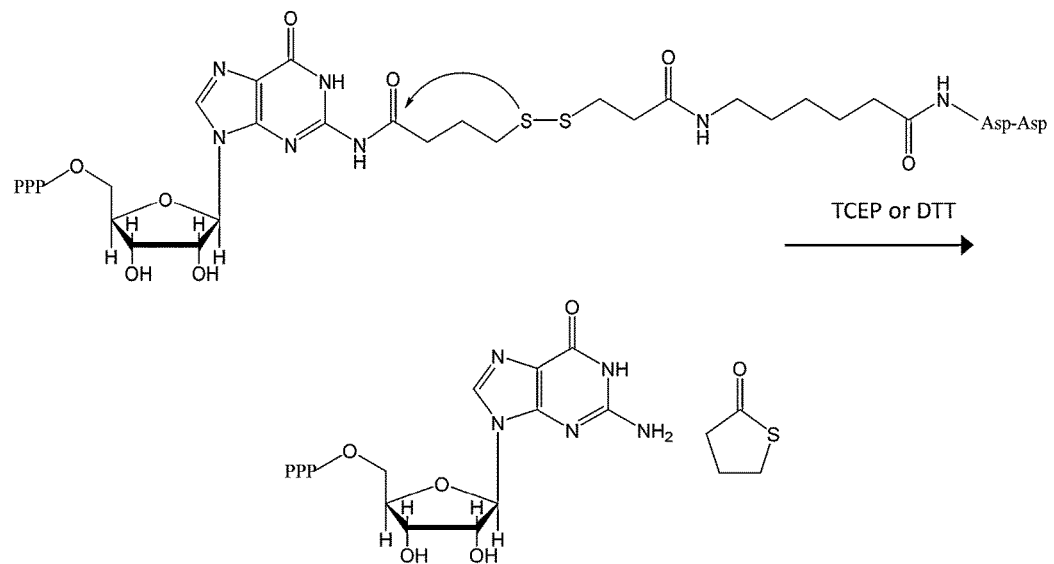
FIG. 9B shows cleavage of the cleavable terminator from a rGTP analog of FIG. 9A to achieve a "natural" rGTP and a cyclic leaving molecule.
Figure 10A:
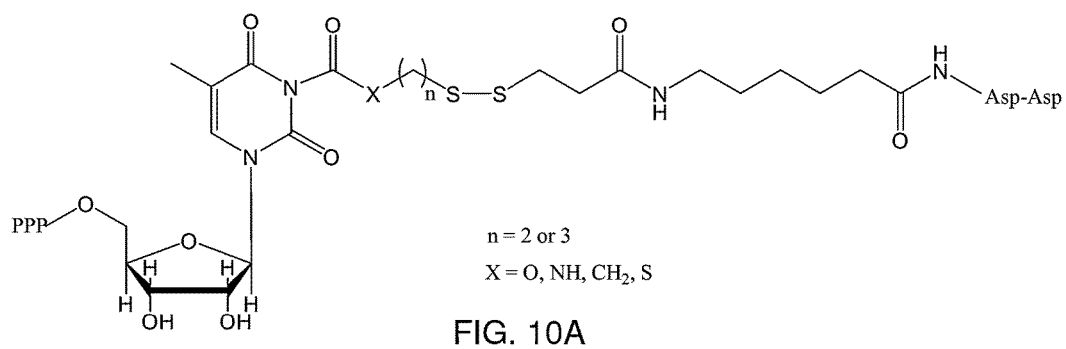
FIG. 10A shows a genus of thymidine triphosphate (rTTP) analogs having a cleavable terminator linked at the N-3 position.
Figure 10B:
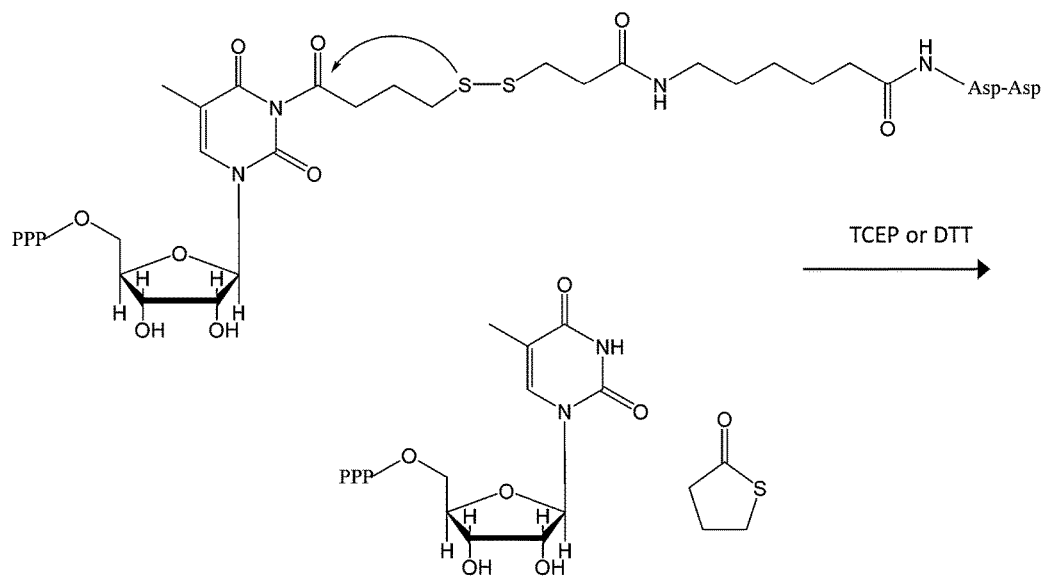
FIG. 10B shows cleavage of the cleavable terminator from a rTTP analog of FIG. 10A to achieve a "natural" rTTP and a cyclic leaving molecule.
Figure 11A:
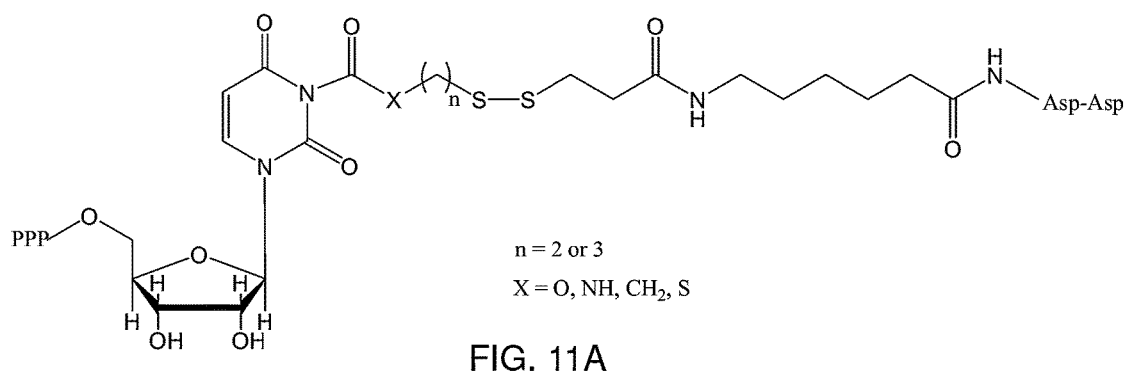
FIG. 11A shows a genus of uridine triphosphate (rUTP) analogs having a cleavable terminator linked at the N-3 position.
Figure 11B:
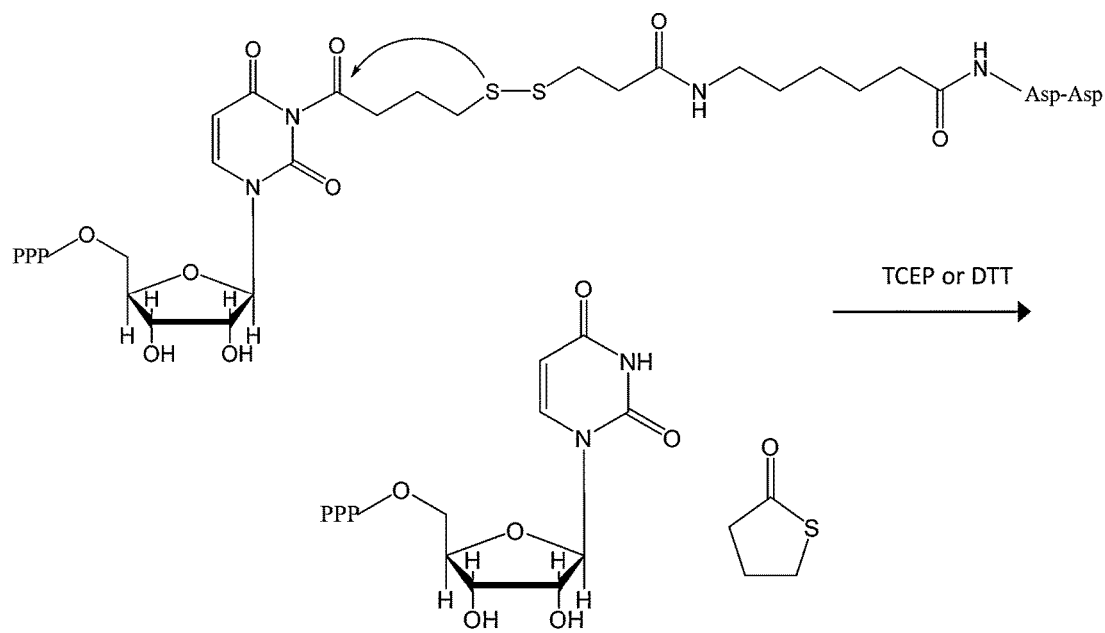
FIG. 11B shows cleavage of the cleavable terminator from a rUTP analog of FIG. 11A to achieve a rUTP and a cyclic leaving molecule.
Figure 13:
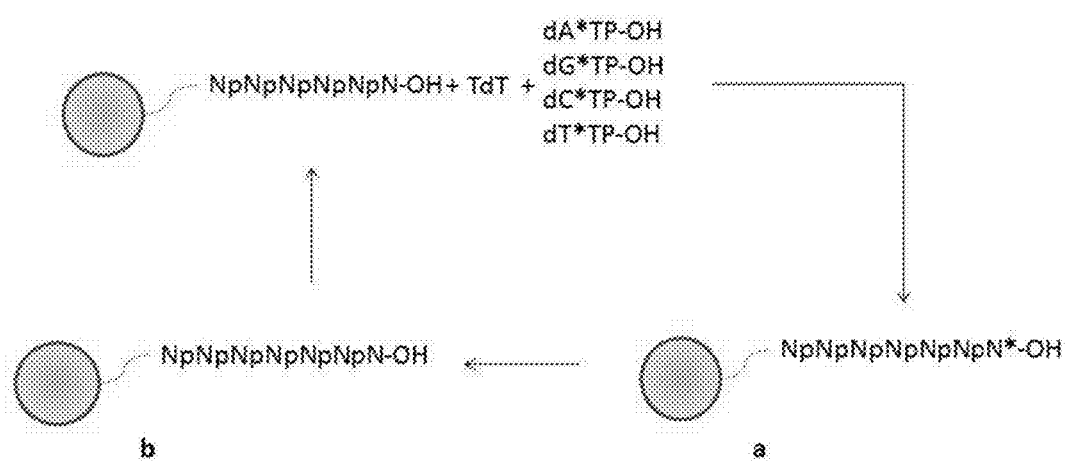
FIG. 13 shows an exemplary terminal deoxynucleotidyl transferase (TdT) mediated polynucleotide synthetic cycle, including: (a) incorporation of a nucleotide triphosphate analog comprising cleavable terminator, dN*TP-OH, and (b) removal of the terminating blocking group (indicated by *), thus enabling the next dN*TP-OH to be incorporated, wherein N=A, G, C, or T.

The methods of the invention can be practiced under a variety of reaction conditions, however the orderly construction and recovery of desired polynucleotides will, in most cases, require a solid support to which the polynucleotides can be grown. In some embodiments, the methods include the enzymatically-mediated synthesis of polynucleotides on a solid support, as illustrated in FIG. 7. When used in conjunction with the cleavable terminator nucleotide triphosphate (NTP) analogs discussed above, it is possible to construct specific polynucleotide sequences of DNA as well as RNA by using, for example, TdT or poly(A) polymerase in an aqueous environment. As shown in FIG. 13, the TdT can be used to effect the stepwise construction of custom polynucleotides by extending the polynucleotide sequence a stepwise fashion. As discussed previously, the inhibitor group of each NTP analog causes the enzyme to stop with the addition of a nucleotide. After each nucleotide extension step, the reactants are washed away from the solid support prior to the removal of the inhibitor by cleaving the linker, and then new reactants are added, allowing the cycle to start anew. At the conclusion of n cycles of extension-remove-deblocking-wash, the finished full-length, single-strand polynucleotide is complete and can be cleaved from the solid support and recovered for subsequent use in applications such as DNA sequencing or PCR. Alternatively, the finished, full-length, single-strand polynucleotide can remain attached to the solid support for subsequent use in applications such as hybridization analysis, protein or DNA affinity capture. In other embodiments, partially double-stranded DNA can be used as an initiator, resulting in the synthesis of double-stranded polynucleotides.

Solid supports suitable for use with the methods of the invention may include glass and silica supports, including beads, slides, pegs, or wells. In some embodiments, the support may be tethered to another structure, such as a polymer well plate or pipette tip. In some embodiments, the solid support may have additional magnetic properties, thus allowing the support to be manipulated or removed from a location using magnets. In other embodiments, the solid support may be a silica coated polymer, thereby allowing the formation of a variety of structural shapes that lend themselves to automated processing.

Synthesizers

To capitalize on the efficiency of the disclosed methods, an aqueous phase DNA synthesizer can be constructed to produce desired polynucleotides in substantial quantities. In one embodiment, a synthesizer will include four wells of the described NTP analog reagents, i.e., dCTP, dATP, dGTP, and dTTP, as well as TdT at concentrations sufficient to effect polynucleotide growth. A plurality of initiating sequences can be attached to a solid support that is designed to be repeatedly dipped into each of the four wells, e.g., using a laboratory robot. The robot could be additionally programmed to rinse the solid support in wash buffer between nucleotide additions, cleave the linking group by exposing the support to a deblocking agent, and wash the solid support a second time prior to moving the solid support to the well of the next desired nucleotide. With simple programming, it is possible to create useful amounts of desired nucleotide sequences in a matter of hours, and with substantial reductions hazardous waste. Ongoing synthesis under carefully controlled conditions will allow the synthesis of polynucleotides with lengths in the thousands of base pairs. Upon completion, the extension products are released from the solid support, whereupon they can be used as finished nucleotide sequences.

A highly parallel embodiment could consist of a series of initiator-solid supports on pegs in either 96 or 384 well formats that could be individually retracted or lowered so that the pegs can be indexed to contact the liquids in the wells in a controlled fashion. The synthesizer could thus consist of the randomly addressable peg device, four enzyme-dNTP analog reservoirs in the same format as the peg device (96 or 384 spacing), additional reagent reservoirs (washing, deblocking, etc.) in the same format as the peg device (96 or 384 spacing), and a transport mechanism (e.g., a laboratory robot) for moving the peg device from one reservoir to another in a user programmable controlled but random access fashion. Care must be taken to avoid contaminating each of the four enzyme-dNTP reservoirs since the contents are reused throughout the entire synthesis process to reduce the cost of each polynucleotide synthesis.

In alternative embodiments, the reagents (e.g., nucleotide analogs, enzymes, buffers) will be moved between solid supports, allowing the reagents to be recycled. For example a system of reservoirs and pumps can move four different nucleotide analog solutions, wash buffers, and/or reducing agent solutions between one or more reactors in which the oligonucleotides will be formed. The reactors and pumps can be conventional, or the devices may be constructed using microfluidics. Because of the non-anhydrous (aqueous) nature of the process, no special care needs to be taken in the design of the hardware used to eliminate exposure to water. The synthesis process can take place with only precautions to control evaporative loss. A highly parallel embodiment could consist of a monolithic series of initiator-solid supports on pegs in either 96 or 384 well format that can be interfaced to a series of wells in the same matching format. Each well would actually be a reaction chamber that is fed by four enzyme-dNTP analog reservoirs and additional reagent reservoirs (washing, deblocking, etc.) with appropriate valves. Provisions would be made in the fluidics logic to recover the enzyme-dNTP reactants in a pristine fashion after each extension reaction since they are reused throughout the entire synthesis process to reduce the cost of each polynucleotide synthesis. In other embodiments, a system of pipetting tips could be used to add and remove reagents.

After synthesis, the released extension products can to be analyzed by high resolution PAGE to determine if the initiators have been extended by the anticipated number of bases compared to controls. A portion of the recovered synthetic DNA may also be sequenced to determine if the synthesized polynucleotides are of the anticipated sequence.

Because the synthesizers are relatively simple and do not require the toxic components needed for phosphoramidite synthesis, synthesizers of the invention will be widely accessible for research institutions, biotechs, and hospitals. Additionally, the ability to reuse/recycle reagents will reduce the waste produced and help reduce the costs of consumables. The inventors anticipate that the methods and systems will be useful in a number of applications, such as DNA sequencing, PCR, and synthetic biology.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

The invention claimed is:

1. A method for synthesizing an oligonucleotide, comprising:
exposing a nucleic acid attached to a solid support to a nucleotide analog in the presence of a nucleotidyl transferase enzyme and in the absence of a nucleic acid template, thereby creating an oligonucleotide analog,
wherein the nucleotide analog comprises an unmodified 3' hydroxyl and a cleavable terminating group comprising a charged moiety,
wherein the oligonucleotide analog is not a substrate for said nucleotidyl transferase enzyme when the cleavable terminating group is attached, but the oligonucleotide analog is a substrate for said nucleotidyl transferase enzyme when the terminating group is not attached.

2. The method of claim 1, wherein the charged moiety comprises a negative charge.

3. The method of claim 1, wherein the charged moiety comprises a net negative charge.

4. The method of claim 3, wherein the charged moiety comprises an amino acid.

5. The method of claim 1, wherein the charged moiety comprises a positive charge.

6. The method of claim 1, wherein the charged moiety comprises a net positive charge.

7. The method of claim 6, wherein the charged moiety comprises an amino acid.

8. The method of claim 1, wherein the nucleotide analog comprises a ribose sugar or a deoxyribose sugar.

9. The method of claim 1, wherein the nucleotide substrate comprises a base selected from the group consisting of adenine, guanine, cytosine, thymine, and uracil.

10. The method of claim 1, wherein the oligonucleotide analog comprising the cleavable terminating group is not a substrate for said nucleotidyl transferase enzyme in an aqueous solution having a pH between about 6.5 and 8.5.

11. The method of claim 1, wherein the oligonucleotide analog comprising the cleavable terminating group is not a substrate for said nucleotidyl transferase because of electrostatic interactions between the charged moiety and said nucleotidyl transferase enzyme.

12. The method of claim 1, wherein said nucleotidyl transferase enzyme comprises a protein sequence that is at least about 90% identical to SEQ ID NO. 1, SEQ ID NO. 3, or SEQ ID NO. 5.

13. The method of claim 1, wherein said nucleotidyl transferase enzyme originates from an organism having a nucleotide sequence that is at least about 90% identical to SEQ ID NO. 2, SEQ ID NO. 4, or SEQ ID NO. 6.

14. A method for oligonucleotide synthesis, the method comprising the steps of:
exposing a support-bound nucleic acid that is free of a nucleic acid template to:
a nucleotide analog that comprises a moiety attached thereto by a cleavable linker and having a free 3' hydroxyl, and
a nucleotidyl transferase, thereby incorporating said nucleotide analog into said support-bound nucleic acid to create an oligonucleotide analog wherein the oligonucleotide analog is not a substrate for said nucleotidyl transferase when the moiety is attached but is a substrate for said nucleotidyl transferase when the moiety is not attached;
washing said solid support upon incorporation of said nucleotide analog to remove unincorporated nucleotide analog;
cleaving said cleavable linker; and
repeating said exposing, washing, and cleaving steps in order to synthesize an oligonucleotide.

15. The method of claim 14, wherein said nucleotide analog comprises a base selected from the group consisting of adenine, guanine, cytosine, thymine, and uracil.

16. The method of claim 14, wherein said nucleotide analog and said nucleotidyl transferase are present in the same solution, and said solution is substantially recycled between subsequent exposing, washing, and cleaving steps.

17. An apparatus for synthesizing oligonucleotides with a predetermined sequence in an aqueous environment, comprising:
a first, second, third, and fourth source of nucleotide triphosphate (NTP) reagent and template-independent nucleotidyl transferase enzyme solutions in fluid communication with a solid support, wherein the reagent solutions in the first, second, third, and fourth sources are selected from NTP-adenine, NTP-guanine, NTP-cytosine, NTP-thymine,
wherein at least a portion of the nucleotide triphosphates comprise an unmodified 3' hydroxyl and a cleavable terminating group that, upon incorporation by a nucleotidyl transferase into an oligonucleotide analog, prevents said oligonucleotide analog from being a substrate for said nucleotidyl transferase in the absence of a nucleic acid template and results in the oligonucleotide analog becoming a substrate for said nucleotidyl transferase in the absence of a nucleic acid template upon cleavage of said terminating group.

18. The apparatus of claim 17, wherein the nucleotides are deoxyribonucleotides.

19. The apparatus of claim 17, further comprising a wash reservoir in fluid communication with the solid support.

20. The apparatus of claim 17, further comprising a source of an aqueous deblocking agent in fluid communication with the solid support.

21. The apparatus of claim 17, wherein the nucleotide triphosphate reagents are flowed to the solid support.

22. The apparatus of claim 17, wherein the solid support is moved to the first, second, third, or fourth source of nucleotide triphosphate reagent and enzyme solution.

23. The apparatus of claim 22, further comprising a programmable manipulator configured to move the solid support.

* * * * *